United States Patent
Irimura et al.

(10) Patent No.: US 7,329,739 B2
(45) Date of Patent: Feb. 12, 2008

(54) USE OF LECTIN LIBRARY FOR DISTINGUISHING GLYCOPROTEINS OR CELLS, DIAGNOSING SERUM OR CELLS, OR FRACTIONATING GLYCOPROTEINS OR CELLS

(75) Inventors: Tatsuro Irimura, Tokyo (JP); Keisuke Maenuma, Tokyo (JP); Kunimitsu Komatsu, Tokyo (JP); Ayumi Tachiki, Chiba (JP); Mariko Matsumoto, Kanagawa (JP)

(73) Assignee: Summit Glycoresearch Corporation, Tokyo (JP)

( * ) Notice: Subject to any disclaimer, the term of this patent is extended or adjusted under 35 U.S.C. 154(b) by 0 days.

(21) Appl. No.: 10/524,970

(22) PCT Filed: Aug. 19, 2003

(86) PCT No.: PCT/JP03/10461

§ 371 (c)(1),
(2), (4) Date: Aug. 18, 2005

(87) PCT Pub. No.: WO2004/018513

PCT Pub. Date: Mar. 4, 2004

(65) Prior Publication Data

US 2006/0141525 A1    Jun. 29, 2006

(30) Foreign Application Priority Data

Aug. 20, 2002 (JP) .............................. 2002-239979

(51) Int. Cl.
*C07K 1/00* (2006.01)
*C07K 16/00* (2006.01)
*G01N 33/53* (2006.01)

(52) U.S. Cl. ...................................... 530/396; 436/827
(58) Field of Classification Search ................ 530/396; 436/827
See application file for complete search history.

(56) References Cited

U.S. PATENT DOCUMENTS

| 5,928,895 | A | 7/1999 | Burnham |
| 5,976,535 | A | 11/1999 | Fritzberg et al. |
| 2004/0091938 | A1* | 5/2004 | Irimura et al. ............... 435/7.1 |

FOREIGN PATENT DOCUMENTS

| EP | 0 846 766 A2 | 6/1998 |
| EP | 1 346 730 A1 | 9/2003 |
| EP | 1362910 A1 | 11/2003 |
| JP | 9-506594 | 6/1997 |
| JP | 10-179176 | 7/1998 |
| WO | WO-95/15979 | 6/1995 |
| WO | WO-97/49989 | 12/1997 |
| WO | WO-02/48189 A2 | 6/2002 |
| WO | WO-02/066633 A1 | 8/2002 |
| WO | WO-02/066634 A1 | 8/2002 |

OTHER PUBLICATIONS

Maenuma, et al., "Mutated Plant Lectin Library to Be Used for Glyco-Informatics", (2001) Proc. Natl. Acad. Sci. USA 98. 2222-2225.
Yim, et al., "Mutated Plant Lectin Library Useful to Identify Different Cells", (2001) Proc. Natl. Acad. Sci. USA 98. 2222-2225.
A. Imberty, et al., "An Unusual Carbohydrate Binding Site Revealed by the Structures of Two *Maackia Amurensis* Lectins Complexed with Sialic Acid-containing Oligosaccharides", The Journal of Biological Chemistry, vol. 275, No. 23, Issue of Jun. 9, pp. 17541-17548, 2000.
Schena, et al., "Increased Serum Levels of IgA1-IgG Immune complexes and anti-F(ab')2 antibodies in Patients with Primary IgA Nephropathy", Clin. exp. Immunol. (1989) 77, 15-20.
Komatsu, et al., "Random Extension of Outer Loops of Maackia *Amurensis hemagglutinin* Generated Libraries with Diverse Specificity and Useful to Identify Cell Surface Glycosylation Profiles", Annual Conference of the Society for Glycobiology, 676 (Oct. 2002).
Yim, et al., "Generation of Libraries of Genetically Engineered Plant Lectins with Diverse Carbohydrate Specificities" Abstract, 5th Annual Conference of the Society for Glycobiology 2000, vol. 10, No. 10, pp. 1094-1095.
Schwachtgen, J-L. Supllementary Eurpoean Search Report for International Application No. PCT/JP0310461, Sep. 6, 2006.

* cited by examiner

*Primary Examiner*—Jon D. Epperson
*Assistant Examiner*—Sue Liu
(74) *Attorney, Agent, or Firm*—David G. Conlin; Gregory B. Butler; Edwards Angell Palmer & Dodge LLP

(57) ABSTRACT

It is intended to provide lectins and a lectin library comprising these lectins which are useful in recognizing differences in carbohydrates on cell surface (for example, sugar chains and cell surface glycoproteins) reflecting extremely subtle differences among cells, etc. and thus distinguishing, identifying or fractionating various cells.

3 Claims, 19 Drawing Sheets

Fig. 2

```
         10        20        30        40        50        60
gccatggctacttccaactcaanaccaactcaagtccttcttgccaccttcttaactttc
   M  A  T  S  N  S  K  P  T  Q  V  L  L  A  T  F  L  T  F
         70        80        90       100       110       120
ttccttttgctactcaacaacgtapactcotcagatgagctttcttttaccatcaacaat
 F  L  L  L  N  N  V  N  S  D  E  L  S  F  T  I  N  N
        130       140       150       160       170       180
ttcatgccaaatcaaggcgatctactcttccaaggtgtagccactgtttcaccaacaggg
 F  M  P  N  Q  G  D  L  L  F  Q  G  V  A  T  V  S  P  T  G
        190       200       210       220       230       240
gtattacaacttaccagcgaagaaaacggtcaaccccctggagtattctgttggcagagct
 V  L  Q  L  T  S  E  E  N  G  Q  P  L  E  Y  S  V  G  R  A
        250       260       270       280       290       300
ctatatactgcccctgtgcgcatttgggacagtaccactggcgccgtagcaagcttctcc
 L  Y  T  A  P  V  R  I  W  D  S  T  T  G  A  V  A  S  F  S
        310       320       330       340       350       360
acttccttcacctttgttgtgaaagcagctaggggagcttctgacggtttagccttctttt
 T  S  F  T  F  V  V  K  A  A  R  G  A  S  D  G  L  A  F  F
        370       380       390       400       410       420
cttgcaccacctgattctcagatcccttcgggcagcgtatcgaaatacctaggacttttt
 L  A  P  P  D  S  Q  I  P  S  G  S  V  S  K  Y  L  G  L  F
        430       440       450       460       470       480
aacaactcaaattccgatagttccaaccaaattgttgctgtagagtttgacacttacttc
 N  N  S  N  S  D  S  S  N  Q  I  V  A  V  E  F  D  T  Y  F
        490       500       510       520       530       540
ggccatagttatgatccctgggatccaaattatcgacatatcggaattgatgtcaacggt
 G  H  S  Y  D  P  W  D  P  N  Y  R  H  I  G  I  D  V  N  G
        550       560       570       580       590       600
attgagtcgataaaaactgtgcaatgggattggattaacggcggagttgccttttgctacc
 I  E  S  I  K  T  V  Q  W  D  W  I  N  G  G  V  A  F  A  T
        610       620       630       640       650       660
ataacctatctagctcccaacaaaacgttaatagcatctctagtttacccttccaatcaa
 I  T  Y  L  A  P  N  K  T  L  I  A  S  L  V  Y  P  S  N  Q
        670       680       690       700       710       720
acaagtttcattgtcgctgcttctgttgatttgaagggaatcctccctgagtgggttaga
 T  S  F  I  V  A  A  S  V  D  L  K  G  I  L  P  E  W  V  R
        730       740       750       760       770       780
gttggtttctctgctgccacgggtgctcctaaagcagttgaaaccacgatgttcgttcc
 V  G  F  S  A  A  T  G  A  P  K  A  V  E  T  H  D  V  R  S
        790       800       810       820       830       840
tggtctttcacgtcaactttggaagccaacagccctgctgatgtggataataatgtgcat
 W  S  F  T  S  T  L  E  A  N  S  P  A  D  V  D  N  N  V  H
        850       860       870       880       890       900
atcgcacgttatactgcataatctcgtgagctttcgtatgtattaggtgtttatgtaaat
 I  A  R  Y  T  A  *
        910       920       930       940       950
taaataacaatgaccctgaaataatggttatcggcgcagctatacaaaaat
```

COOH

Fig. 9

|  | 127 | | | | | | | | 135 | | |
|---|---|---|---|---|---|---|---|---|---|---|---|
| wild-type | Asp | Thr | Tyr | Phe | Gly | His | Ser | Tyr | Asp | Pro | Trp |
| clone 1 | Asp | Thr | Tyr | Phe | Gly | His | Gly | Tyr | Asp | Pro | Trp |
| clone 2 | Asp | Thr | Tyr | Phe | Arg | His | Asn | Tyr | Asp | Pro | Trp |
| clone 3 | Asp | Thr | Tyr | Phe | Ser | His | Asn | Tyr | Asp | Pro | Trp |
| clone 4 | Asp | Thr | Tyr | Phe | Gly | His | Arg | Tyr | Asp | Pro | Trp |
| clone 5 | Asp | Thr | Tyr | Phe | Gly | His | Val | Tyr | Asp | Pro | Trp |
| clone 6 | Asp | Thr | Tyr | Phe | Ala | His | Asn | Tyr | Asp | Pro | Trp |
| clone 7 | Asp | Thr | Tyr | Phe | Gly | His | Leu | Tyr | Asp | Pro | Trp |
| clone 8 | Asp | Thr | Tyr | Phe | Gly | His | Asp | Tyr | Asp | Pro | Trp |
| clone 9 | Asp | Thr | Tyr | Phe | Tyr | His | Asn | Tyr | Asp | Pro | Trp |
| clone 10 | Asp | Thr | Tyr | Phe | Gly | His | Trp | Tyr | Asp | Pro | Trp |

Fig. 17
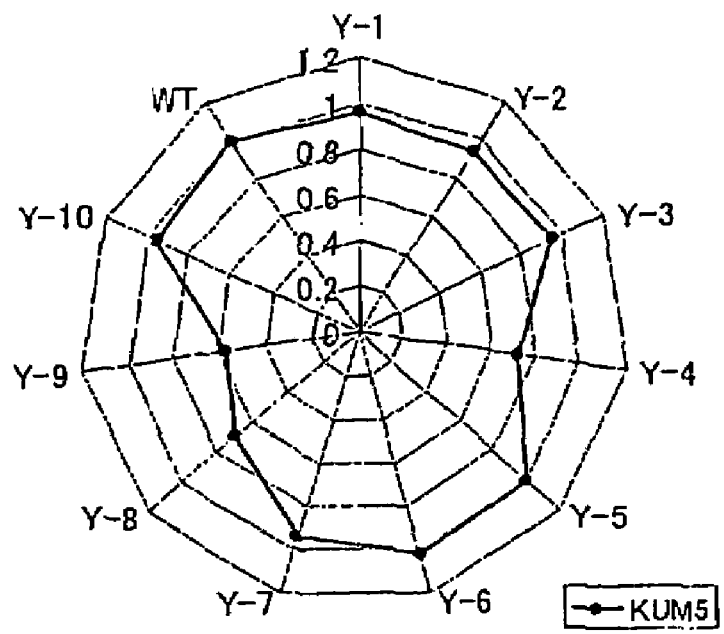
A  Loop C erythrocyte panning
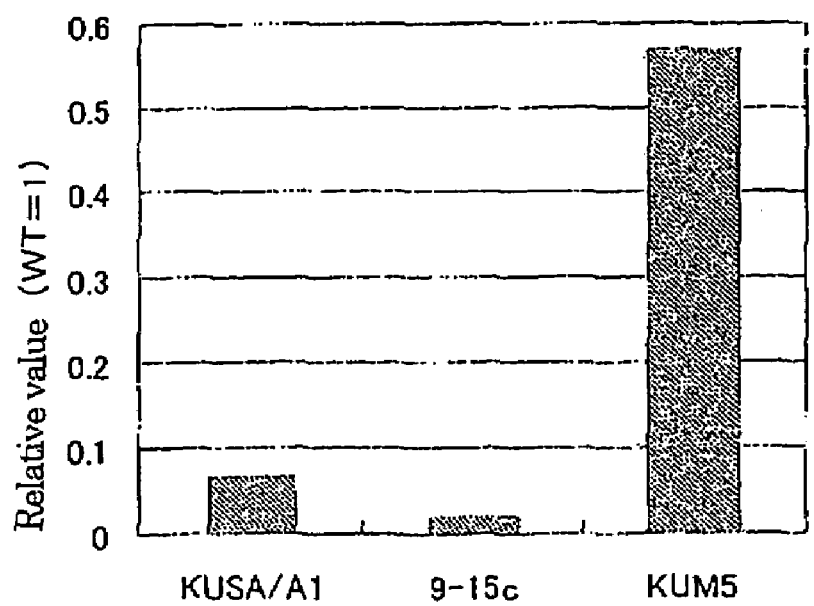
B

USE OF LECTIN LIBRARY FOR DISTINGUISHING GLYCOPROTEINS OR CELLS, DIAGNOSING SERUM OR CELLS, OR FRACTIONATING GLYCOPROTEINS OR CELLS

TECHNICAL FIELD OF THE INVENTION

The present invention relates to a method of selecting lectins having certain predetermined analysis ability from plural kinds of lectins, as well as lectins selected by the method.

BACKGROUND ART

In recent years, sugar chain engineering has been remarkably developing and has been revealing the mechanisms where sugar chains in macromolecules such as plant cell wall proteoglycans contributing to stabilization of cells, glycolipids having an influence on the differentiation, growth, adhesion and movement of cells, and glycoproteins involved in intercellular interaction and recognition of cells regulate highly accurate biological reactions with their functions mutually exchanged, assisted, amplified, controlled or inhibited. Sugar chains on cell surfaces, occurrence of diseases due to an abnormality in sugar chain/receptor interaction, or the role of sugar chains in viral infection such as AIDS are being extensively studied.

Particularly, sugar chains that cells have on their surfaces can be utilized for discriminating and identifying certain cells from other cells, for example normal cells from cancer cells, or different cells in their differentiation stage. For example, there have been many reports that sugar chains varies in cancer cells depending on their malignancy, or varies in stems cells depending on their differentiation stage. Accordingly, the analysis (e.g. discrimination and identification) of sugar chains is considered very important in distinguishing, identifying and fractionating cells.

Utilization of lectins having a binding activity to specific sugar chains (carbohydrates) is considered to bring many merits as a means of analyzing carbohydrates on cell surface, represented by such sugar chains. However, at present, the type of naturally occurring lectins is limited, and there are not utilized enough types of lectins for analyzing particularly sugar chains as described above. That is, discriminating subtle differences in sugar chains, etc., is very important in analysis of carbohydrates, including analysis of sugar chains. Therefore, it is a key task in this analysis that various kinds of lectins having specificities to enable discrimination of carbohydrates can be prepared sufficiently and systematically.

DISCLOSURE OF INVENTION

The present invention provides lectins and lectin libraries comprising these lectins which are useful in recognizing differences in carbohydrates on cell surface (for example, sugar chains and cell surface glycoproteins) reflecting extremely subtle differences among cells, etc. and thus distinguishing, identifying or fractionating various cells.

Particularly in the present invention, lectins having a desired analysis ability are selected from plural kinds of lectins by panning with specific cells etc. as an indicator or by another method. One or more lectins thus selected can be used to analyze cells etc. The selected lectins can be utilized as a diagnostic medicine or a diagnostic kit. It was revealed that among the lectins thus selected, there are lectins binding very strongly and specifically to specific cells which cannot be separated by another means. The present invention provides fractionation of cells etc. by the lectins, as well as a method of plasmapheresis by utilizing the lectins.

Accordingly, the first aspect of the present invention is concerned with a lectin library for distinguishing glycoproteins or cells, diagnosing serum or cells or fractionating glycoproteins or cells, which comprises at least one kind of lectin selected from plural kinds of lectins, on the basis of affinity for cells, pseudo-cells, glycoproteins or sugar chains serving as an indicator.

It was found that the cells etc. serving as an indicator do not have to be cells themselves as the subject of discrimination, diagnosis and fractionation. That is, even if specific lectins in the present invention are selected not on the basis of their affinity for the same cells as the subject of discrimination, but on the basis of their affinity for cells etc. related in a certain trait to the subject of discrimination, the selected lectins can achieve the intended object. This means that complete knowledge on sugar chains (carbohydrates) of the subject of discrimination is not always necessary for preparing the library of the present invention.

For example, a lectin library used in discrimination of IgA or osteoblast can prepared on the basis of affinity for erythrocyte or glycophorin as an indicator. This library is useful for selection of lectins recognizing O-binding sugar chains present on IgA and osteoblast. Particularly, the library composed of lectins thus selected was revealed to be preferably usable in discrimination of IgA glycoform and in discrimination of osteoblast subfamily. Other lectin libraries were also revealed to be preferably usable in discrimination of cell subfamily derived from mesenchymal stem cells or in discrimination of cancer cell metastasis.

Another aspect of the present invention relates to a method wherein the interaction between lectin and a sample to be examined is indicated by another substance having an affinity for the sample.

That is, the result of discrimination of cells by the lectin library prepared in the manner described above can be indicated by, for example, other additional specificity for the cells etc., such as antigen/antibody reaction.

A further aspect of the present invention is to provide a diagnostic kit comprising the lectin library described above.

That is, the lectin library of the present invention can be utilized as a kit in an arbitrary form, and non-restrictive examples thereof include diagnostic reagents, lectin chips and various sensors.

The final aspect of the present invention is to provide a method wherein the lectin library of the present invention containing at least one kind of lectin is used as a means of fractionation/separation of cells.

It was surprisingly found that in preparation of the lectin library of the present invention, there are lectins having a high specificity and a high affinity for specific cells. The fractionation/separation or removal of the cells by the lectins could thereby be efficiently achieved. Accordingly, the lectin library of the present invention was revealed to be applicable to plasmapheresis etc.

BRIEF DESCRIPTION OF THE DRAWINGS

FIG. 2 shows the nucleotide sequence of cDNA (SEQ ID NO: 1) encoding MAH and its predicted amino acid sequence (SEQ ID NO: 2). In the amino acid sequence in FIG. 2, the position of loop D is shown by the third underline (lowest underline), and in this loop, particularly 5 amino acids considered to exert a significant influence on binding to sugar chains are enclosed with a square. In the figure, I indicates an Xho I (ctcgag) restriction enzyme site, II indicates a Bgl II (agatct) restriction enzyme site, and III indicates an Spe I (actagt) restriction enzyme site.

FIG. 9 shows amino acid sequences (SEQ ID NOS 38, and 22-31, respectively in order of appearance) of lectins contained in a lectin library used in discrimination of IgA different in sugar chain glycoform and in discrimination of cell subgroup derived from mesenchymal stem cells.

FIG. 17A shows a pattern of binding of KUM5 cells (subgroup of mesenchymal stem cells) to the lectin library, and FIG. 17B shows comparison in binding of other subgroups (KUSA-A1 and 9-15C) to Y-9 lectin in the library.

BEST MODE FOR CARRYING OUT THE INVENTION

Lectin

In the present invention, plural kinds of lectins are composed of naturally occurring lectins and/or artificial lectins.

The naturally occurring lectins in the present invention include animal lectins, vegetable lectins and other lectins. Preferable non-restrictive examples of naturally occurring lectins include vegetable lectins, particularly lectins of the legume family, and more preferable examples of lectins of the legume family include those derived from *Maackia amurensis* hemagglutinin (MAH).

The artificial lectins include lectins synthesized by known chemical techniques, but are preferably lectins produced by bioengineering techniques. Particularly, lectins obtained by genetically modifying naturally occurring lectins can be preferably used. Particularly preferable genetic modification can be achieved by manipulating DNA in a specific region of the lectin gene, but is not limited thereto.

Specific regions subjected to DNA manipulation include a region encoding a sugar chain binding (recognition) site of naturally occurring lectin, and in the DNA manipulation, the amino acid sequence of a sugar chain binding site of lectin is subjected to deletion, substitution and/or addition in such a range that the sugar chain binding activity of the site is not completely deteriorated.

Figure 1A:
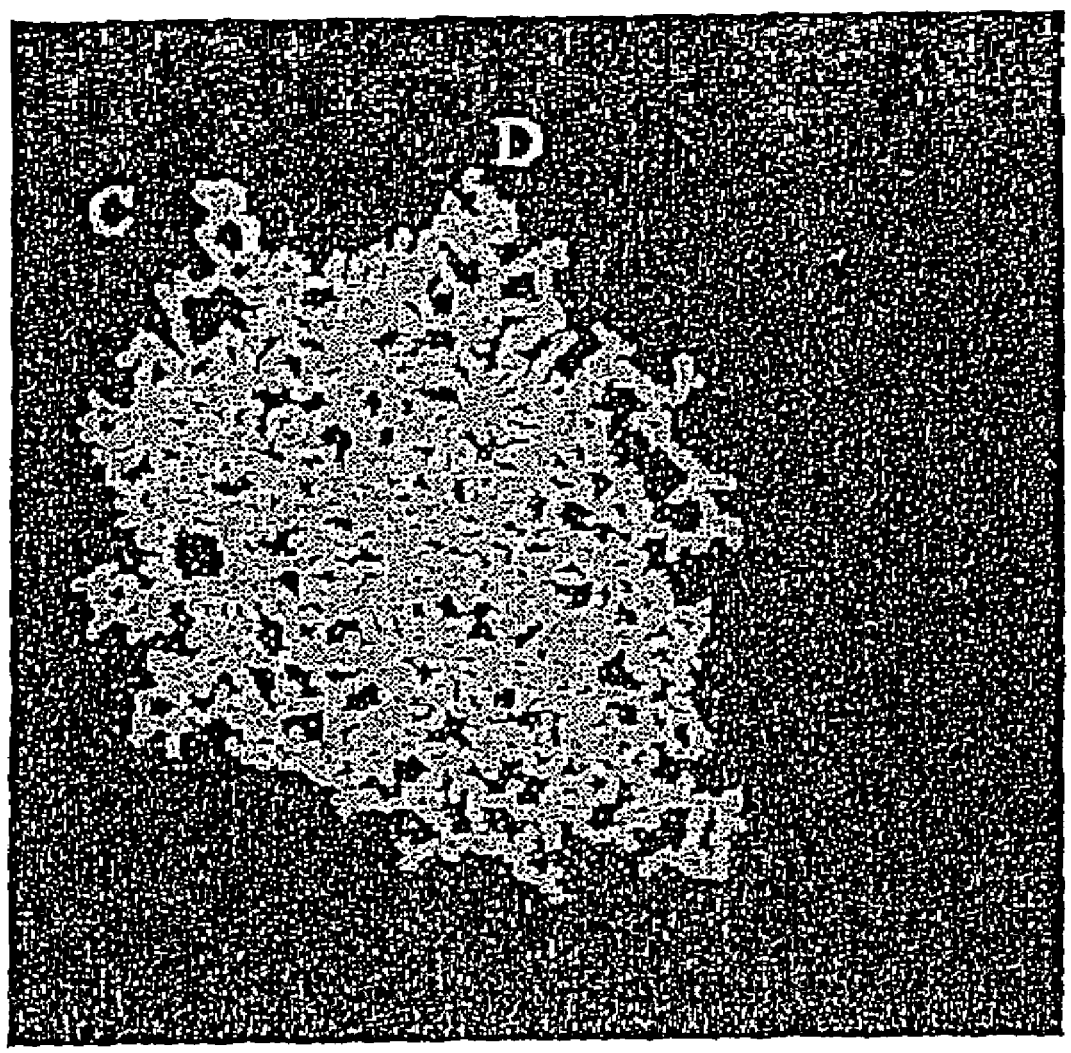
FIG. 1A shows a stereostructure of MAH model.
Figure 1B:
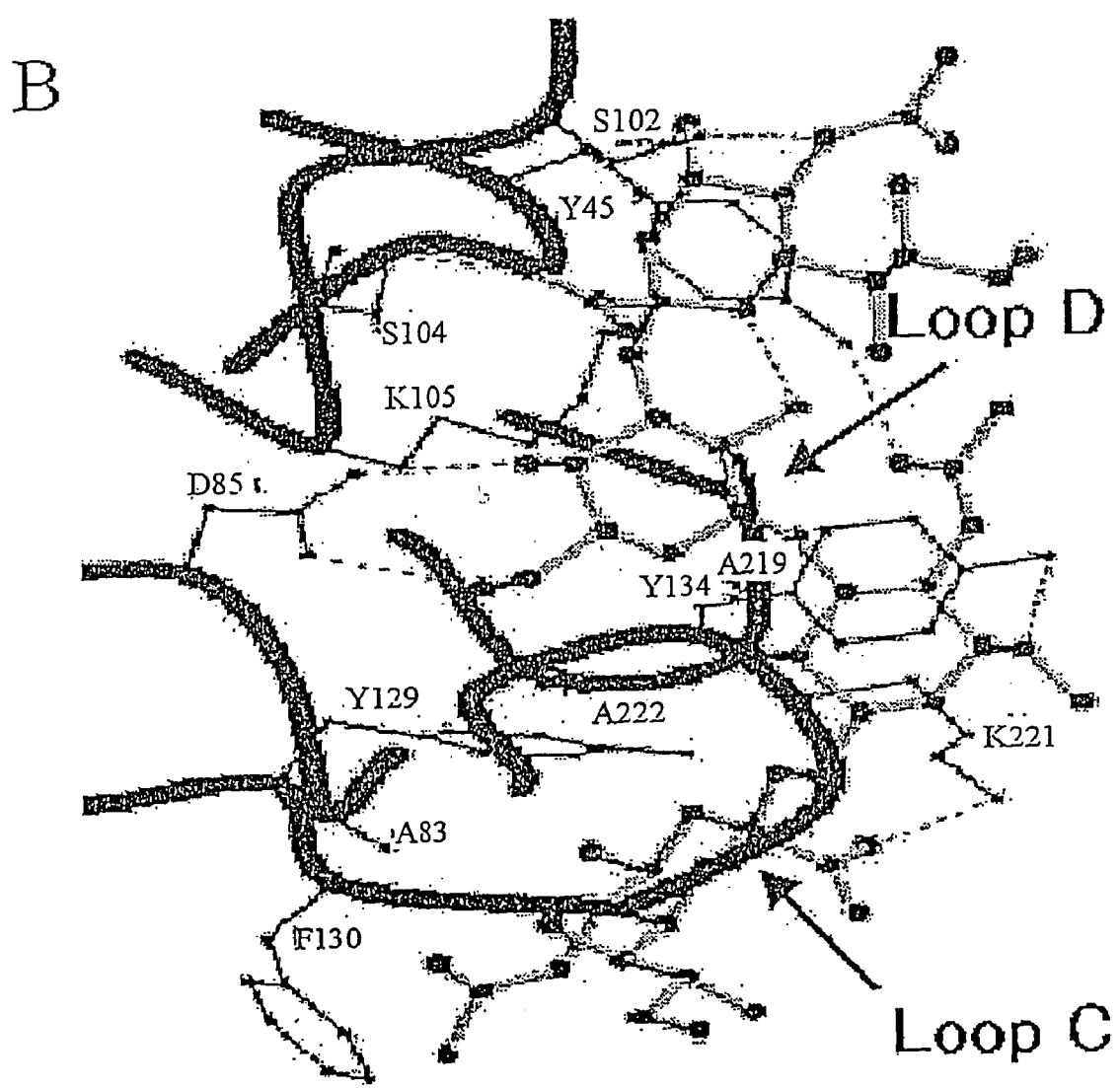
FIG. 1B illustrates a stereostructure of MAH. In the figure, loops C and D are considered to sandwich a sugar chain therebetween thereby binding to a predetermined sugar chain, thus recognizing differences among sugar chains.
Figure 1C:
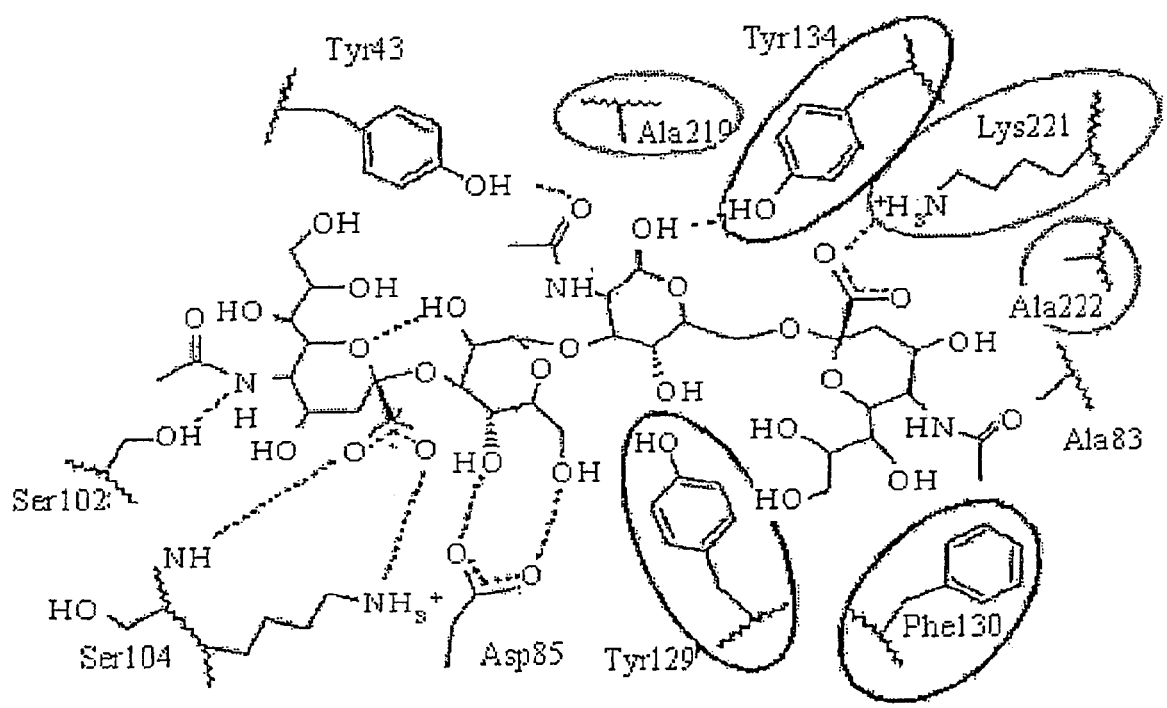
FIG. 1C shows the binding of sugar chains to MAH.
Figure 3:
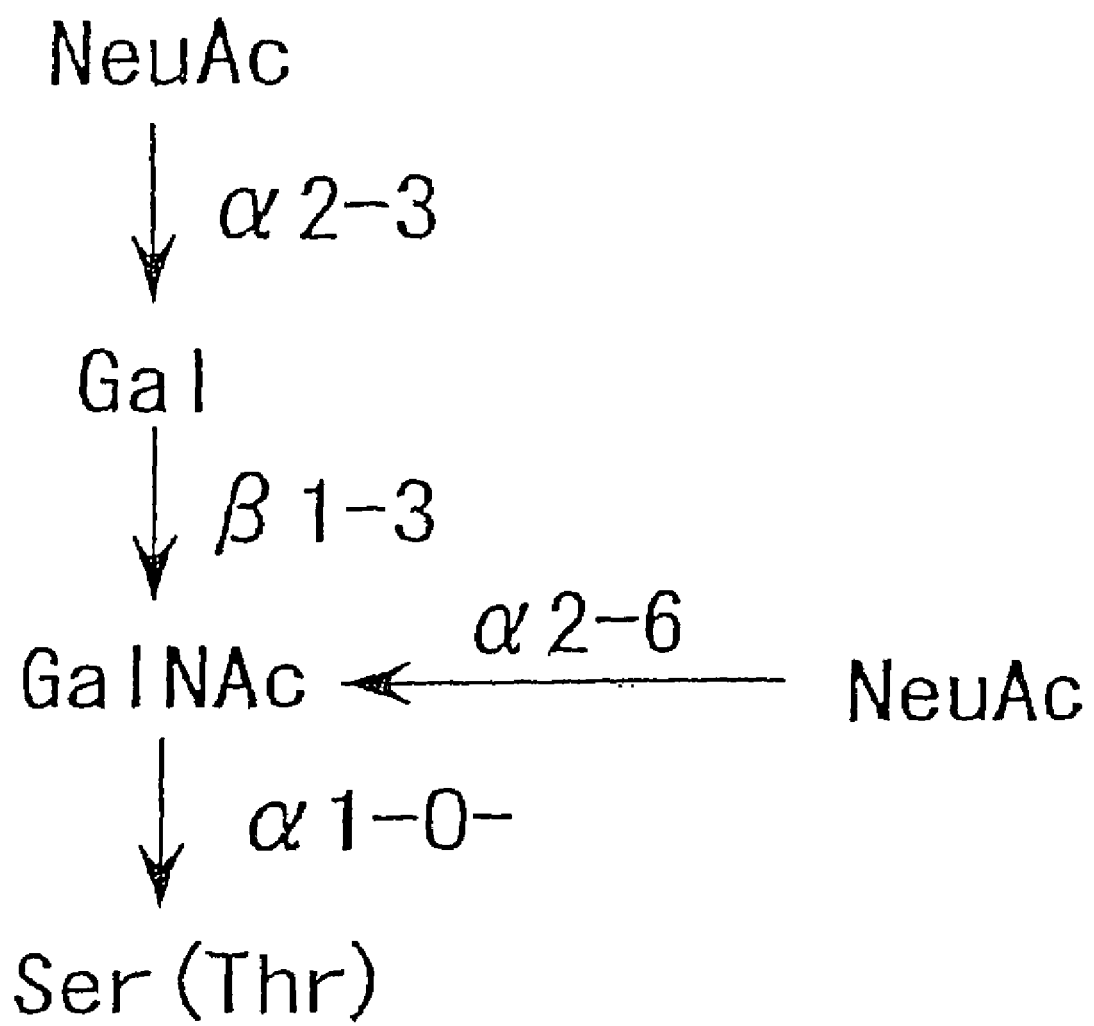
FIG. 3 shows a sugar chain structure recognized by wild type Maackia aurensis lectin (Maackia amurensis hemagglutinin (MAH)).

Such DNA manipulation can be designed from analysis of a stereostructure of lectin. FIGS. 1A and 1B illustrate a stereostructure of MAH lectin, and FIG. 1C shows the binding the lectin to sugar chains. From these figures, it can be seen that loops C and D in the figure sandwich a sugar chain therebetween thereby forming a sugar chain recognition and binding site. Accordingly, DNAs encoding loops C and D as the sugar chain recognition site can be the subject of manipulation. In the MAH lectin, loops A and B are also present (not shown in the figures), and DNA regions encoding these loops can be preferable as the subject of DNA manipulation.

More specifically, in the nucleotide sequence and amino acid sequence of MAH lectin shown in FIG. 2, the nucleotide sequence 466 to 498 (amino acid sequence 127 to 137) corresponds to loop C, and the nucleotide sequence 721 to 780 (amino acid sequence 212 to 231) corresponds to loop D. Accordingly, these regions may be contained as a target region to be modified. Non-restrictive examples of modification of loop C include insertion of amino acid into an amino acid sequence in positions 127 to 137 as shown in FIG. 5 and random modification to specific amino acids with other amino acids fixed as shown in FIG. 6. The modification to loop D can be exemplified by insertion or substitution in the amino acid sequence 219 to 224 as shown in FIG. 15. In this specification, the nucleotide sequence is numbered from the initiation codon, and the amino acid sequence is numbered from the N-terminal amino (Met) acid residue.

In lectins of the legume family other than MAH, loops A, B, C and D are similarly present, and are estimated to participate in sugar-chain recognition/binding, and can thus be the subject of modification.

Selection of Lectins

In the present invention, one or more kinds of lectins useful for intended sugar chain analysis are selected from plural kinds of lectins and used to prepare a lectin library. The prepared lectin library can be used to identify carbohydrates themselves represented by sugar chains, or cells and glycoproteins having sugar chains (carbohydrates).

For selection of the lectins, arbitrary techniques can be used, but it is advantageous to use panning utilizing cells, pseudo-cells or glycoproteins having a specific sugar chain, or the sugar chain itself or its arbitrary structural unit. Each of plural kinds of lectins, or a lectin mixture containing plural kinds of lectins, may be subjected to panning. The cells, pseudo-cells, sugar chain (including monosaccharides) etc. used in panning can reflect traits as a key of serum, cells and glycoproteins to be discriminated, diagnosed or fractionated by the lectin library of the present invention.

That is, in preparation of the library for the purpose of distinguishing a specific differentiated state of cells, cells capable of reflecting the specific differentiated state can be used in panning, and in this panning, detailed knowledge on sugar chains of the cells is not always necessary.

For example, for the purpose of preparing a lectin library usable in identification or profiling of a subgroup of cells having an ability to be differentiated from human bone marrow cells to specific cells or in predicting properties of the cells, a plurality of lectins may be used in panning with human erythrocyte.

Figure 8:
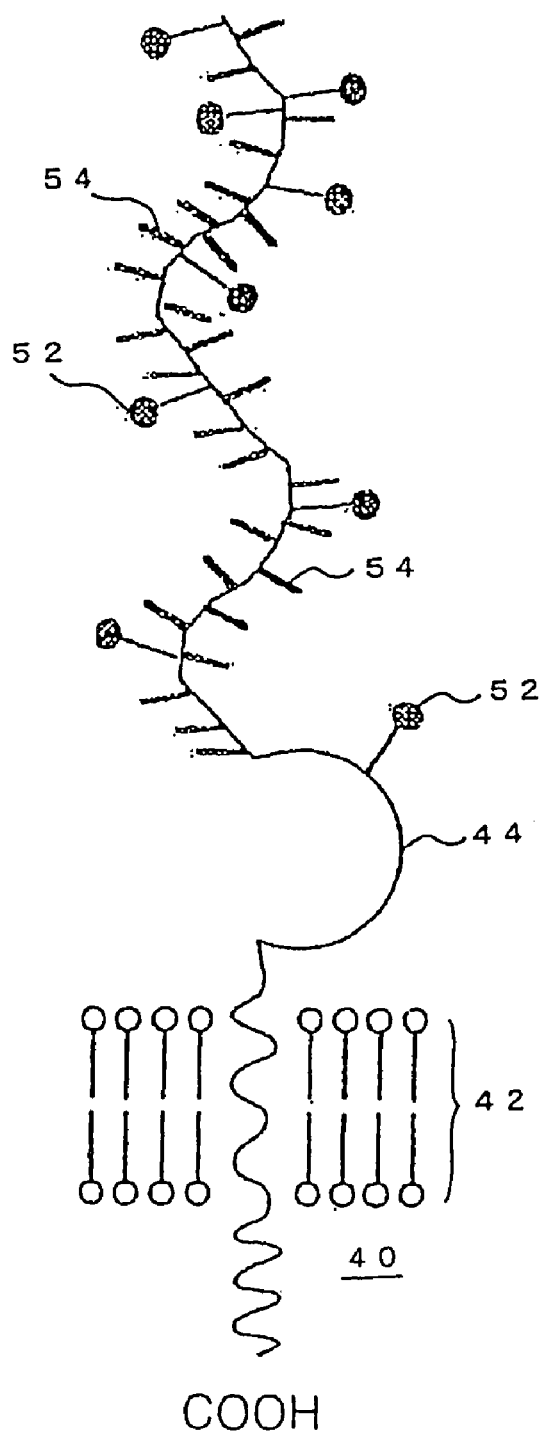
FIG. 8 illustrates sugar chains expressed on cell surface. A transmembrane protein is inserted into cell membrane 42 of cell 40, and is outgoing to the outside of the cell. O-binding sugar chain 52 and N-binding sugar chain 54 are bound like leaves to the outgoing protein. A glycoprotein glycophorin expressed on erythrocyte membrane has a very similar structure.

Cells having an ability to be differentiated from human bone marrow cells into myocardial cells have a stem cell-related antigen called CD34, and the CD34 is known as a glycoprotein called mucin (which will be described in detail later). In human CD34, there are 260 extracellular amino acid residues including the N-terminus, and an O-binding sugar chain is added thereto. Threonine (T) and serine (S), that is, amino acids to which the sugar chain can be added, are populated particularly from the N-terminus to position 144. That is, human CD34 has, in this region, a sequence of repeated T/S such as TTT and STS, which is regarded as a structure characteristic in mucin-like glycoprotein (FIG. 8).

The structure of sugar chains in human CD34 is similar to that of human erythrocyte, and thus human erythrocyte may be used in panning for selecting lectins constituting a lectin library in distinguishing cells expressing the CD34 and having an ability to be differentiated from human bone marrow cells to myocardial cells, for example in distinguishing 9-15C cells from KUSA/A1 cells having an ability to be differentiated into bone marrow cells.

Figure 4:
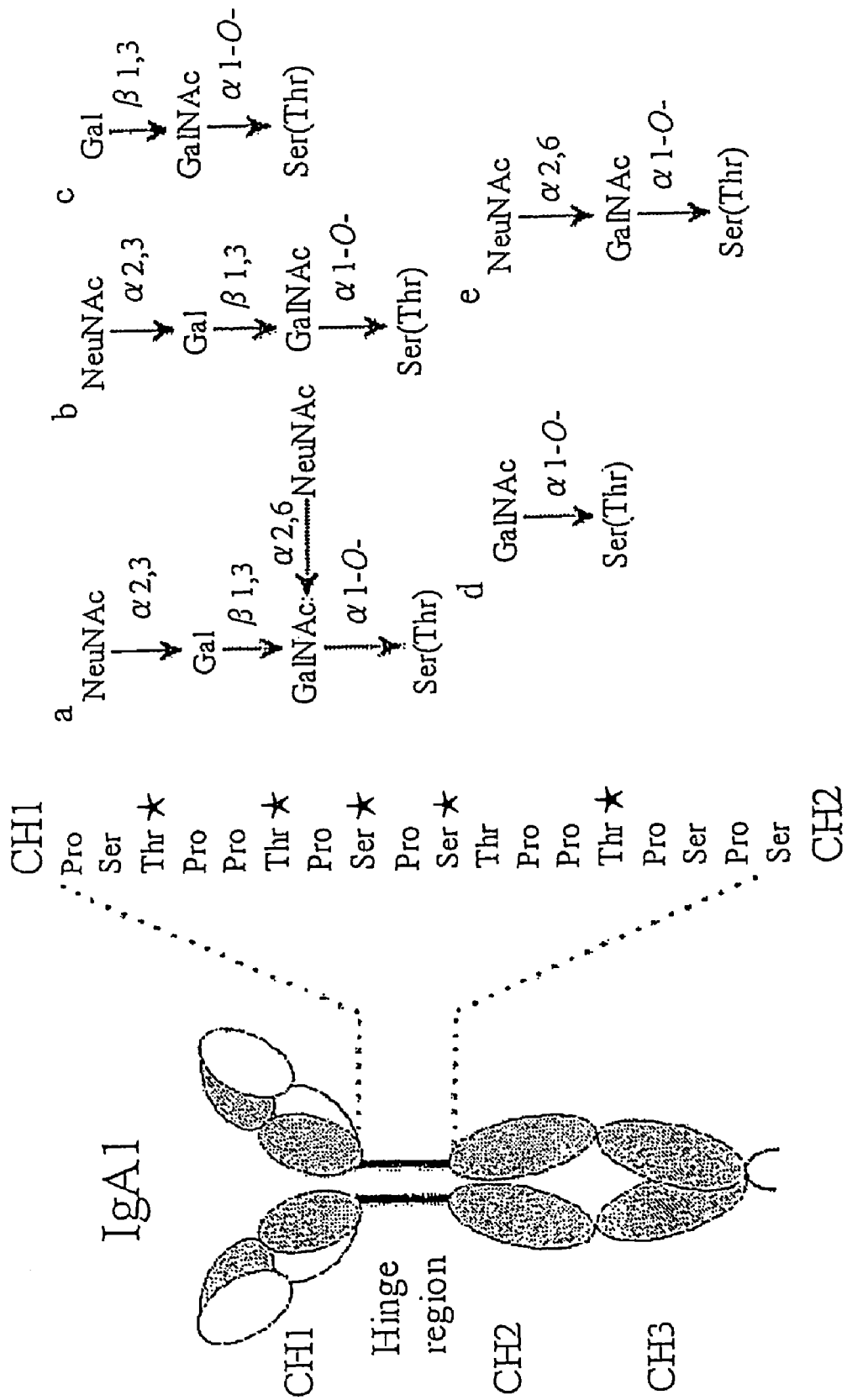
FIG. 4 is an illustration of varieties of IgA1 sugar chain structures (SEQ ID NO: 34).
Figure 5:
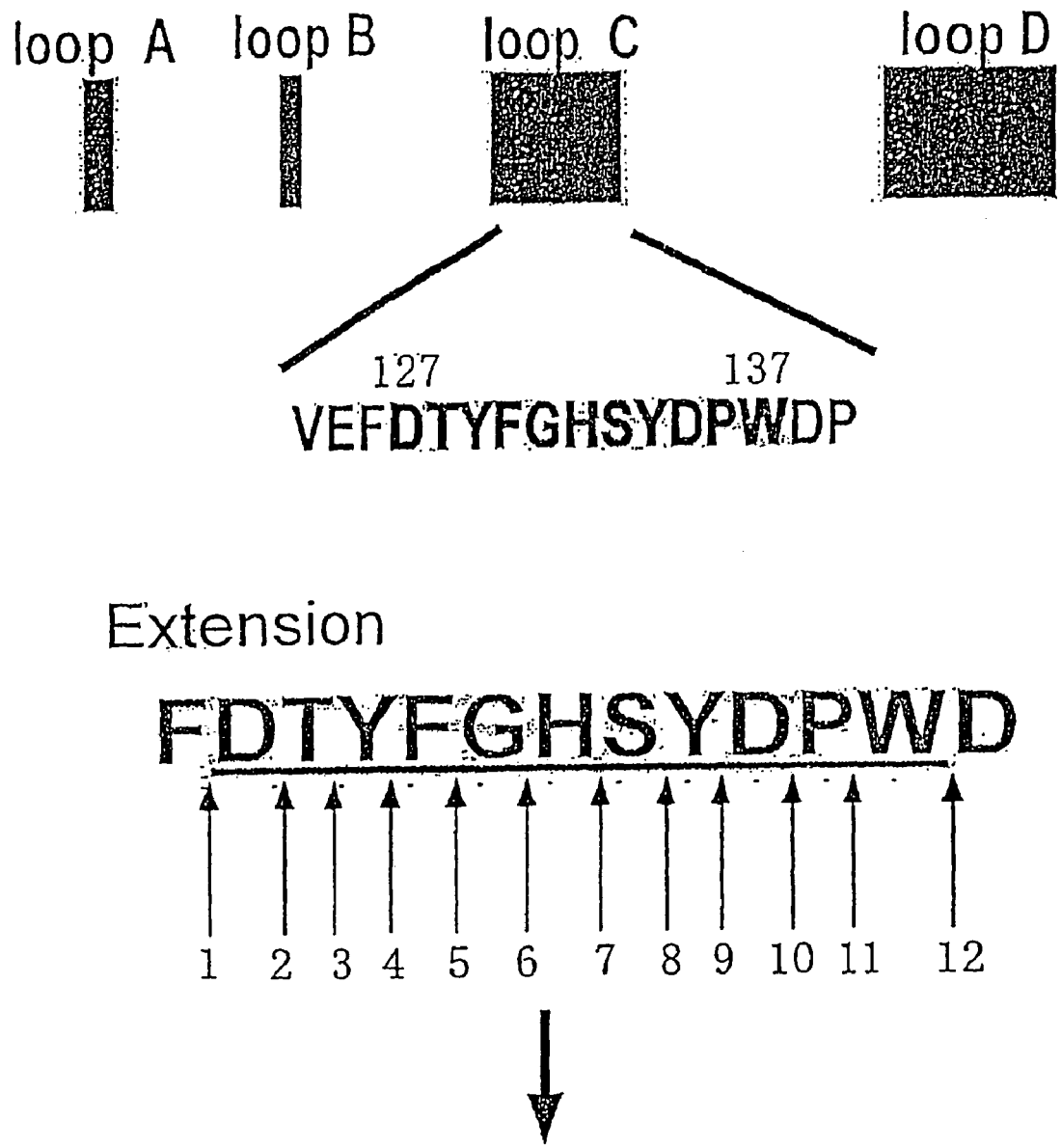
FIG. 5 shows the amino acid sequence of MAH loop C wherein the position of amino acid inserted by modification is indicated (SEQ ID NOS 35-37, respectively in order of appearance).
Figure 6:
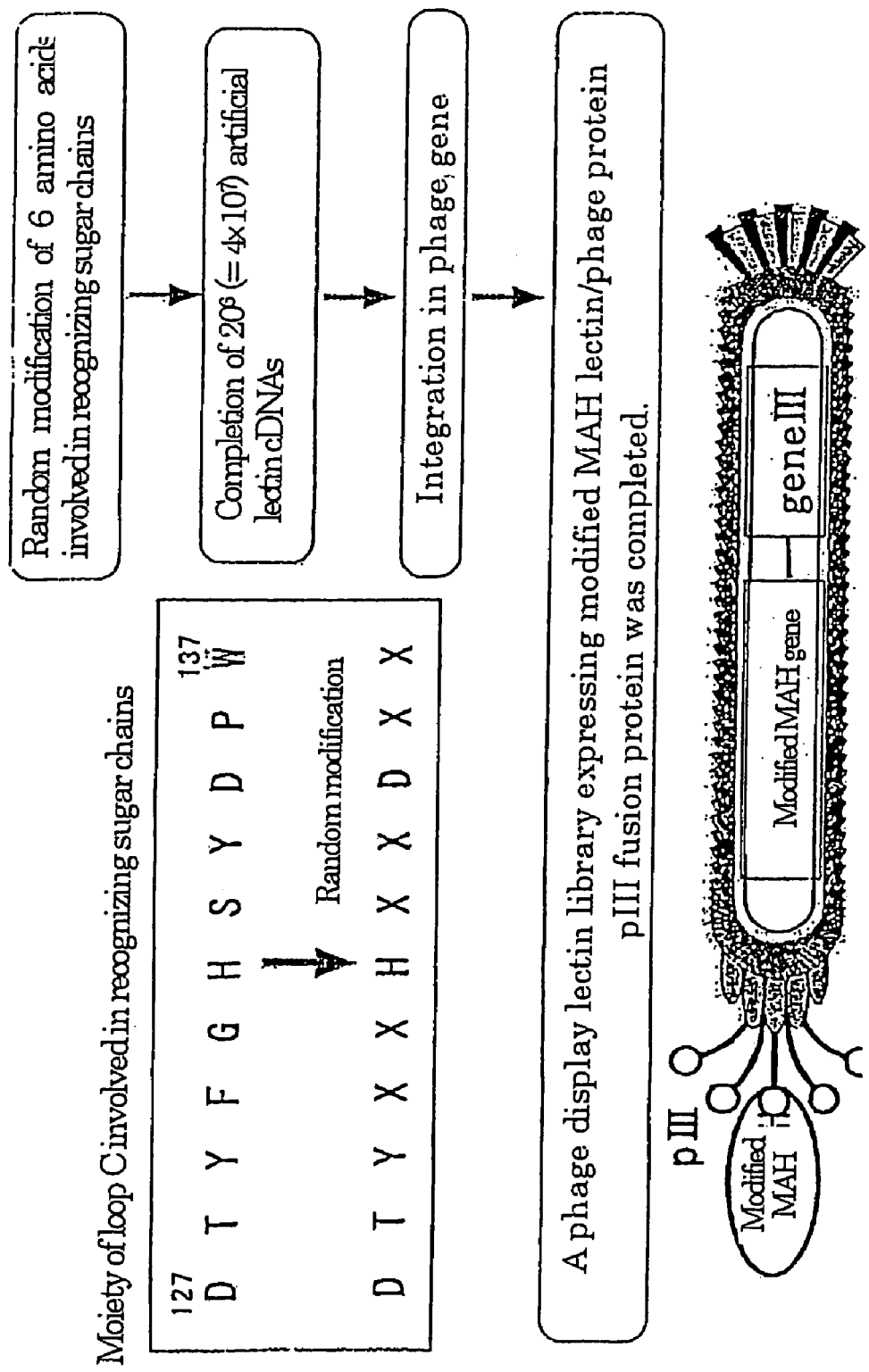
FIG. 6 shows an outline of a phago display lectin library (SEQ ID NOS 38-39, respectively in order of appearance).
Figure 7:
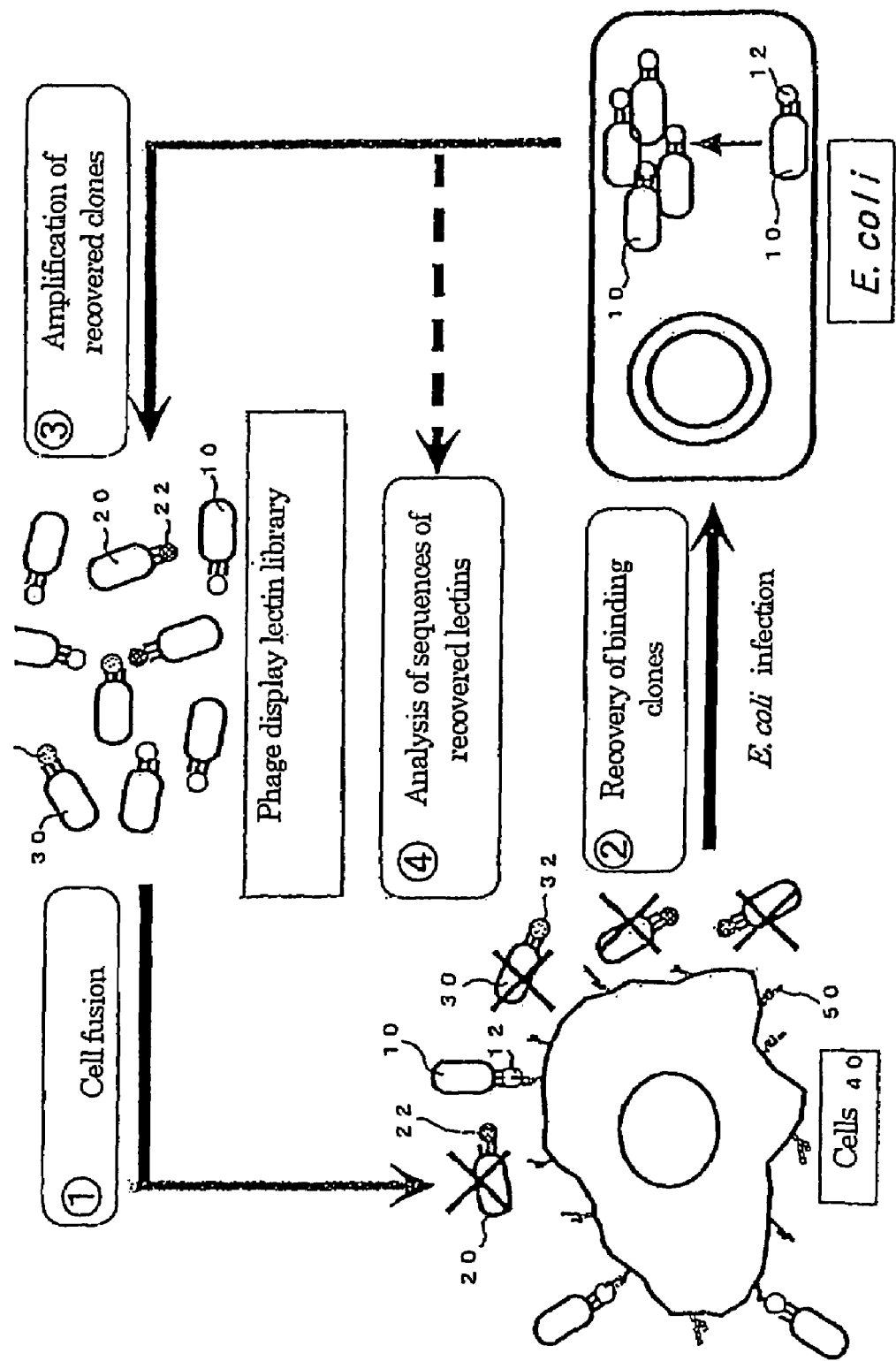
FIG. 7 shows a procedure of recovering artificial lectins by panning.

Similarly, IgA1 molecule has, in its hinge amino acid sequence, threonine (T) and serine (S) to which an O-binding sugar chain is added (FIG. 4). By analysis with mass spectrometry, it is reported that sugar chains added to IgA1 molecules in patients with IgA nephropathy are sugar chain-deficient IgA1 molecules lacking in sialic acid and galactose as compared with those in healthy persons. On one hand, a glycoprotein called glycophorin, wherein sialic acid-containing O-binding sugar chains are added in a cluster to a peptide, is present in human erythrocyte, and has a structure of a sugar chain/peptide complex near the IgA1 hinge. Accordingly, a lectin library for distinguishing IgA glyco-form can be prepared from lectins selected from a collection of lectins by panning with human erythrocyte.

Various methods other than panning can be used in selection as described above. Selection involves not only selection from a single lectin collection but also formation of a lectin library by suitable combination of one kind or predetermined kinds of lectin collections. For example, one kind of genetically modified lectin is formed by inserting one (one kind of) amino acid into a predetermined position (for example, loop D in MAH lectin) and then stocked. Similarly, another kind of lectin can be formed by inserting another kind of amino acid into the same position and stocked. By changing the insertion position, more kinds of lectins can be selected depending on type and stocked. These lectins are considered similar in characteristics, but differences among the characteristics can be revealed by various tests. By suitably blending such lectin stocks having functions specified depending on type, a lectin library suitable for distinguishing cells etc. can be similarly prepared. At least one lectin exhibiting affinity for or binding to one or more cells etc. to be distinguished should be present in lectins constituting the lectin library of the present invention, and it is more preferable that when two or more cells are to be distinguished, a lectin having high affinity for or high binding to all of the two or more cells is further contained. It is further more preferable that a lectin having low affinity for or low binding to the two or more cells to be distinguished is further contained. This is because by comparing them, discrimination of cells etc. can be accurately conducted. The lectin library containing the necessary type and number of lectins can be preferably used in the present invention.

Use of the Library

The lectin library prepared in the manner described above can be used in distinguishing glycoproteins or cells, in diagnosing serum or cells, or in fractionating glycoproteins or cells, and can be used advantageously in distinguishing differences among sugar chains particularly in a morbid state.

For example, mucin is a major glycoprotein in mucus with which lumens of digestive tracts such as trachea, stomach and intestines and gonads are covered. Mucin has a large number of O-binding sugar chains bound via O-glycoside bonds to a polypeptide (core protein, apomucin). In many cases, mucin has many repeated sequence domains. These repeated sequence domains are rich in serine and threonine residues to almost all of which O-binding sugar chains are added in the case of competed mucin.

The relationship between sugar chains expressed on MUC1 mucin and malignant behavior accompanying the progress of cancer is also suggested, and a lectin library capable of distinguishing such sugar chains is considered useful. For example, it is reported that as the expression of sugar chain sialyl Lewis X antigen expressed on MUC1 mucin in colon cancer is increased, infiltration with cancer cells occurs to increase malignancy, and the amount of sialyl Lewis X antigen expressed is reversely correlated with the degree of survival for 5 years (Cancer Research 53, 3632-3637, Aug. 1, 1993), and the lectin library of the present invention can be effective in distinguishing the malignancy.

Further, changes in sugars on a mucin-containing cellular cortex are recognized as a feature of malignant transformation of cells in cancer. These changes are believed to participate in change in cellular adhesion, in abnormal behaviors of cancer cells such as metastasis, and in demolishment of immune protection. Accordingly, if the degree of modification of sugar chains in the glycoprotein mucin could be measured by the library of the present invention, the malignancy of specific cancer cells would be distinguished and predicted.

The role of sialic acid in the mucin structure is important particularly in cancer metastasis, and the MAH recognizing a structure of O-binding sugar chain containing sialic acid and its genetically modified lectin can be used as a lectin library to achieve the diagnosis of serum or cells with respect to cancer metastasis.

On one hand, there is also an attempt at judging the malignancy of cancers by an antibody to mucin. However, a monoclonal antibody has a high specificity for a specific mucin antigen, but the expression of sugar chains as the antigen is regulated strictly by time and space in each stage of differentiation of each tissue, and accordingly, techniques by the monoclonal antibody merely give information on the sugar chains at a certain point of time. By observing changes with time and in qualities and in the amount of sugar chains by the lectin library capable of distinguishing the type of sugar chain and the degree of specificity, not only diagnosis of morbid state but also efficient early diagnosis, prognosis and therapy can be achieved.

Sugar chains depending on morbid states such as infection, inflammation, cancer, mental disorder, Alzheimer's disease etc. are not limited in the mucin described above. Diseases accompanied by changes in N-binding sugar chains and diseases accompanied by changes in sugar chains of other glycoproteins or glycolipids are also reported, and the lectin library capable of distinguishing the type of sugar chain and the degree of specificity is considered useful in examining changes with time and in qualities and in the amount of sugar chains.

In addition, the library of the present invention is also useful for the purpose of fractionating specific glycoproteins or cells. For this purpose, a library consisting of only one kind of lectin can be sufficient. In particular, some lectins selected from lectins produced through genetic modification were found to have a very high affinity for specific cells, and such lectins can be used singly or in combination thereof to efficiently fractionate specific glycoproteins and cells. This fractionation can also be applied to plasmapheresis.

As described above, the lectin library of the present invention is useful for discrimination, diagnosis and fractionation of various cells etc., and particularly the library has been revealed to be applicable to discrimination of IgA glycoform, cancer cells different in metastasis, and a cell population derived from mesenchymal stem cells, and these applications constitute preferable examples of use of the lectin library of the present invention.

Kit and Apparatus

The lectin library of the present invention can be applied to prepare various diagnostic kits and apparatuses. For example, an apparatus for distinguishing cells etc. can be produced by immobilizing lectins in the lectin library of the present invention in a suitable order in predetermined positions on a substrate. The region on which the lectin is immobilized may be like a well or a mere spot. The substrate may be composed of any materials having any shapes, such as chip, plate and bead, insofar as lectins can be immobilized thereon.

It is preferable that when a plurality of lectins are to be immobilized on the substrate, the lectins are arranged and immobilized so as to display a clear discrimination pattern. For example, a plurality of lectins which bind, with varying affinity, to sugar chains on cell surface are immobilized in a specific arrangement, whereby discrimination results can be easily judged from the arrangement pattern.

Such arrangement is particularly effective in forming diagnostic kits or apparatuses as chips or various sensors, and these can be produced by suitably changing known procedures of producing DNA chips.

As a matter of course, the positions where individual lectins are to be immobilized on a chip are suitably changed so as to be optimize the diagnosis of objective cells or diseases. The substrate made of the materials described above may contain synthetic resin (including plastics), metal (including platinum, silver, copper, gold, silicon etc.), mica and a mixture thereof.

On one hand, the kit can be provided in the form of a reagent containing the lectin library of the present invention, and a method of preparing such reagent can be achieved by standard techniques for those skilled in the art. Binding of lectin to a sample, for example, binding of lectin to a specific cell can be detected by previously labeling lectin or the cell, and then measuring a label in the lectin/cell conjugate, or without particularly labeling the two, the presence or amount of the lectin/cell conjugate may be determined by using an antibody recognizing another epitope of the cell.

Alternatively, in a more complex mode, an anti-sample antibody to be immobilized on a solid support, the lectin library of the present invention and a labeled anti-lectin antibody can constitute a kit of the present invention. In the kit, the anti-sample antibody is immobilized on wells etc. and then a sample to be measured is brought into contact with the antibody to form an antibody/sample conjugate, and then the lectin of the present invention is added to, and bound to, the sample, and finally the bound lectin is detected by the labeled anti-lectin antibody.

Other variations can be practiced, and such variations would be easily understood by those skilled in the art.

Accordingly, kits of the present invention can contain additional reagents other than the lectin library, and the additional reagents can be substances preferably having affinity other than lectin/sample interaction, for example substances having an affinity based on antigen/antibody reaction.

When the library of the present invention is used as the kit in a specific form other than the reagent, detection may be carried out by staining a sample or by labeling a sample with labeled fluorescence, or by measuring a change in mass or electricity in intramolecular interaction. The change in mass in intramolecular interaction may be measured by a quartz radiator balance or by surface plasmon resonance. Alternatively, after the analysis of sugar chains of glycoprotein by the lectin library, the protein of the glycoprotein may be fluorescence-labeled with a secondary antibody, or after an irradiation of the protein of the glycoprotein with a pulse laser, the ionized protein may be detected by a mass analyzer. As a matter of course, these techniques may be combined.

As an example of the chip, plural kinds of lectins from the lectin library of the present invention are immobilized in predetermined positions to form lectin-immobilized regions containing different kinds of lectins, and for example a serum sample is allowed to flow thereon to contact the sample with the lectins. After serum glycoproteins in the sample not binding to the lectins or not having substantial binding force are washed away, a binding marker is bound to a structure other than the sugar of the bound and immobilized serum glycoprotein. An excess of the marker is washed away, and the serum can be discriminated by judging the marker upon coloration or the like.

Alternatively, an antibody having a property of binding to a structure other than the sugar chain of serum glycoprotein is immobilized, and a serum sample or the like is allowed to flow thereon thereby contacting with the antibody to immobilize an antigen (e.g., serum glycoprotein) against the antibody, while antigens (serum glycoproteins) not binding or substantially not binding to the antibody are washed away, and then various lectins for distinguishing the sugar chain structure of the bound and immobilized serum glycoprotein are bound thereto, and after an excess of the lectins are washed away, the serum can be distinguished by judgment upon coloration etc.

When a sample is immobilized, on the other hand, a distinguishing agent containing the lectin library is allowed to flow thereon, and a marker unique to each lectin can be used (for example, a tag is attached to the lectin by genetic engineering, and coloration etc. of the tag or a binding marker unique to tag is used) to specify the type of the bound lectin thereby distinguishing and diagnosing the samples.

Hereinafter, the present invention is described in more detail by reference to specific examples and drawings, but the present invention is not limited to the examples.

EXAMPLES

Outline

At least a part of a region regarded as being related to 3a sugar binding site of *Maackia amurensis* hemagglutinin (MAH) that is a sialic acid-containing sugar chain-specific lectin of the legume family was randomly modified by a genetic engineering method, and from the randomly modified lectins, a plurality of artificial lectins capable of distinguishing variations of a plurality of different sugar chains were prepared. From the collection of artificial lectins thus obtained, lectins capable of distinguishing different kinds of cells by a binding pattern to the cells are selected by using predetermined cells etc., to prepare one lectin library. This lectin library could be used to establish a screening system for selecting lectins specific to biologically important sugar chains. It is known that various complex carbohydrates having slightly different structural structures are present on mammalian cells. Formation of lectins capable of distinguishing such various structures is considered very useful. This lectin library can recognize a carbohydrate sequence whose sugar chain is a sialic acid residue, that is, a sequence consisting of Neu5Acα2-3Galβ1-3 (Neu5Acα2-6)GalNAc (4). Another isolectin engineering *Maackia amurensis* leukoagglutinin (MAL) can specifically recognize a sequence of Neu5Acα2-3Galβ1-4GlcNAc (5), and both the lectins are unique among legume lectins and other lectins. MAH has a relative molecular mass of 29,000, and consists of a subunit dimer. The nucleotide sequence of cDNA encoding MAH and an amino acid sequence deduced therefrom indicate that MAH is composed of 287 amino acids, and contains 30 amino acid single peptides. An estimated sugar chain recognition domain of MAH has been identified by study of old by comparing its amino acid sequence with an amino acid sequence of another lectin (7) of the legume family and by study of old by genetic modification of a domain defined by these amino acids conferring the binding property on MAH. From a computer model of a 3-dimensional structure of MAH containing Neu5Acα2-3Galβ1-3 (Neu5Acα2-6)GalNAc (8), these observations were confirmed.

Example 1

[Acquisition of a Lectin Library of Loop C-Modified Lectins by Panning with Erythrocyte]

In MAH lectin, loop C was randomly modified. In an amino acid sequence corresponding to a sugar chain recognition site of loop C in MAH, Asp127, His32 and Asp135 which were considered necessary for recognizing sugar chains and for maintaining the structure of lectin were preserved without mutation.

[Production of Loop C-Modified MAH]

After it was confirmed that MAH lectin was expressed on phage to agglutinate crythroeyte, the sugar chain recognition site of loop C in MAH was modified randomly by AmpliTaq Gold DNA polymerase (manufactured by PE Biosystems) in a Perkin-Elmer 2400 thermal cycler. The primer and reverse primer used therein are shown in Table 1.

TABLE 1

Primers

Primer (containing an Eco RI site)
(SEQ ID NO: 32)
5'-CCGGAATTCGACACTTACNNKNNKCATNNKNNKGATNNKNNKGACCC
AAACTACAGACATATC-3'

Reverse primer (containing a Bam Hi site)
5'-CACAAACGAATGGGGATCCAC-3' (SEQ ID NO: 19)

To obtain a PCR product, the following protocol was used. First, a reaction at 95° C. for 9 minutes and 30 cycles (each consisting of reactions at 94° C. for 1 minute, at 54° C. for 1 minute and at 72° C. for 1 minute) were carried out. The product was treated with an excess of restriction enzymes Eco RI and Bam HI.

The product was ligated to EcoRI/BamHI-digested wild type MAH-pComb3 phagemid (pComb3 phagemid vector having wild type MAH cDNA)).

[Preparation of Phage]

MAH lectin-pComb3 was incorporated into *E. coli* SURE 2 cell (manufactured by Stratagene, La Jolla, Calif.). The cells were cultured on a HEM plate containing 50 μg/ml carbenicillin (24 g/L trypton, 48 g/L yeast extract, 10 g/L MOPS, pH 7.0) at 37° C. for 8 hours. The cells were dipped in 10 ml HEM, then released and recovered. The HEM medium containing the cells was cultured in 100 ml HEM, pH 6.9 (supplemented with 1 mM $CaCl_2$ and 1 mM $MnCl_2$)/carbenicillin) for 1 to 2 hours. The cell suspension was regulated to an $A_{600}$ of about 0.3, and the cultured cells were infected with VSCM13 helper phage (about $10^{12}$ pfu, manufactured by Stratagene, La Jolla, Calif.). The phage with which the cells had been infected was cultured at 30° C. for 12 hours under shaking, and isolated from the culture by precipitation overnight with polyethylene glycol 8000 and NaCl at 4° C. After the separation by centrifugation, the resulting phage pellet was suspended in Tris-buffered saline (TBS: 50 mM Tris-HCl, pH 7.5 containing 150 mM NaCl)+ 1% bovine serum albumin (BSA)).

[Panning with Human Erythrocyte]

Human erythrocyte was used in panning. About $10^{12}$ pfu phage was added to a suspension of 5 μl human erythrocyte in 600 μl TBS containing 1% BSA, and cultured at 4° C. for 5 hours under stirring. The cells were recovered as a pellet and washed twice with 1 ml TBS at 4° C. 2 ml Sure cells ($OD_{600}$=1) were added to the final cell pellet containing the phage, and cultured. After the culture at 37° C. for 15 minutes, the *E. coli* cells were transferred onto multiple HEM (pH 7.0)/carbenicillin plates and cultured at 37° C. for 8 hours. From a supernatant of the *E. coli* cell culture, a phage suspension was prepared, and this procedure was repeated 3 times.

[Sequencing of DNA of Modified Lectin and Introduction of Flag Peptide]

$2.74 \times 10^7$ clones were obtained by the first panning, and $1 \times 10^9$ clones were obtained after the third panning. 288 clones were selected at random and their amino acid sequences were determined. And it was found that 10 clones (FIG. 9, Y1 to Y10) had amino acid sequences different from that of wild type MAH.

Each modified MAH cDNA-pComb3 was subjected to PCR with a sense primer N-Flag-Xhol (5'-CCAGGT-GAAACTGCTCGAGTCAGATG-3', SEQ ID NO: 20) and an antisense primer N-Flag-BgIII (5'-TCCACCGCCA- GATCTCTATGCAGTGTAACG-3', SEQ ID NO: 33). The resulting PCR product was recovered with a PCR Purification Kit (manufactured by QIAGEN) and treated with restriction enzymes Xho I And Bgl II. The product thus treated was ligated to XhoI/BgIII-digested pFlag-ATS (manufactured by Sigma). Each plasmid thus obtained was incorporated into E. coli JM109.

[Expression of Flag Fusion Protein]

The E. coli JM109 containing the known expression plasmid was cultured at 37° C. for 3 hours in an HEM medium containing 1 mM $CaCl_2$, $MnCl_2$, 20 mM $MgCl_2$. After the expression of a flag fusion protein was induced with isopropyl-β-D-thiogalactoside (IPTG: final concentration, 1 mM), the E. coli was further cultured at 37° C. for 3 hours. The cultured E. coli was centrifuged at 9600 rpm to give a pellet which was then suspended in TBS (Tris-buffered saline). This suspension was subjected 5 times to freezing on liquid nitrogen and thawing on a water bath at 37° C. The resulting suspension was centrifuged at 15000 rpm at 4° C. for 30 minutes. A supernatant containing the flag fusion protein was taken and quantified for its protein by a BCA protein assay kit (manufactured by PIERCE).

Example 2

[Discrimination of IgA Glycoform]

One example wherein the lectin library was applied to an IgA glycoform identification method is described below in the order of procedures.

1) A genetically modified lectin library wherein the amino acid sequence of a sugar chain recognition site of MAH lectin (Maackia aurensis lectin) was modified is prepared.
2) Lectins having a high affinity for IgA from patients with IgA nephropathy are selected by panning to prepare a lectin sub-library.
3) From the lectin sub-library obtained in 2) above, lectins well reflecting differences between IgA from patients with IgA nephropathy and IgA from healthy persons are selected if necessary, and immobilized on a microtiter plate to prepare a lectin plate.
4) Discrimination of glycoforms of IgA by the lectin library: Patterns of binding of the IgA from patients with IgA nephropathy and the serum IgA from healthy persons to the lectin plate are compared and analyzed.
5) Examination of serodiagnosis assay: Sugar chains are added enzymatically and chemically to commercial IgA from healthy persons, to prepare an artificial IgA. The artificial IgA is mixed with serum from healthy persons, and then analyzed for pattern with the lectin plate. The assay conditions are optimized by examining the influence of other serum proteins present in serum.

Figure 11:
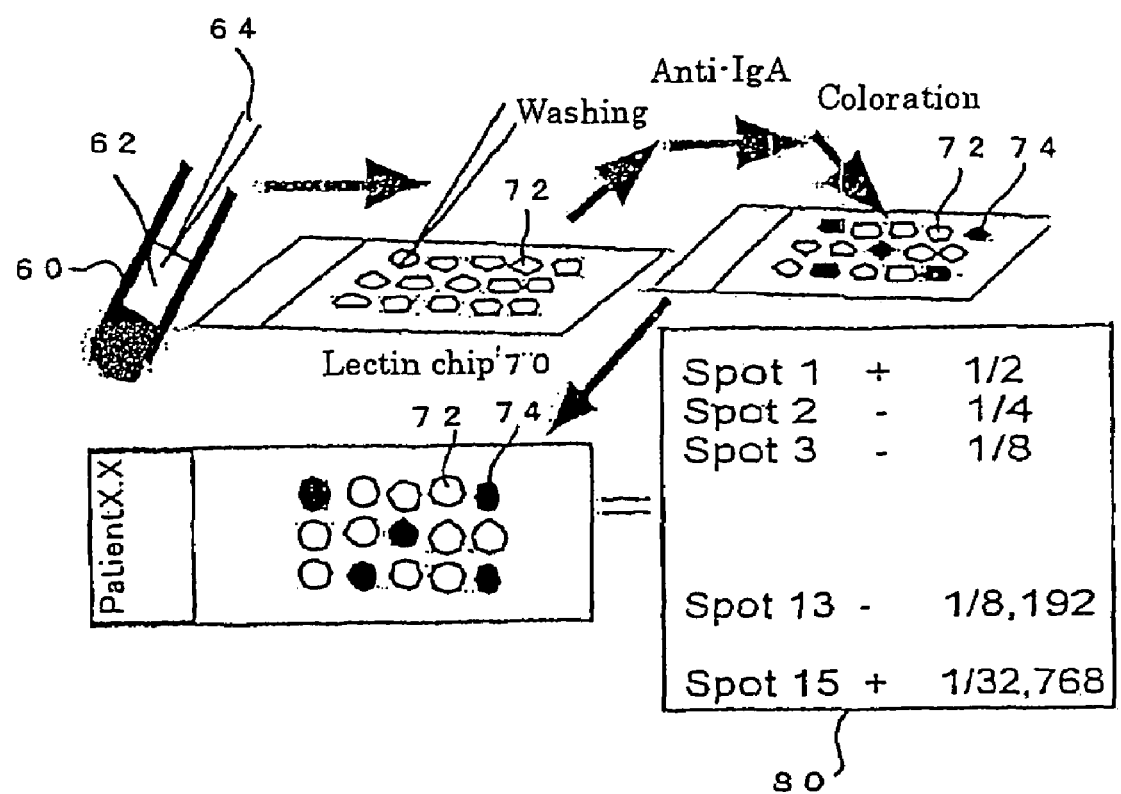
FIG. 11 shows one example of a lectin chip and a method of using the same lectin chip (with respect to IgA).

Now, the mechanism of this method is described in more detail. In the IgA hinge where abnormalities in O-binding sugar chains are observed in patients with IgA nephropathy, O-binding sugar chains can be added to 5 sites where serine or threonine residues are present in the amino acid sequence of the IgA hinge, and there are 6 patterns of O-binding sugar chains, and thus there are theoretically $6^5$ (that is, 7,776) O-binding sugar chain positions or sugar chain structures in the hinge region. It is difficult to examine each possible position or structure by conventional complex sugar chain analysis, but the pattern analysis by ON/OFF of lectins recognizing O-binding sugar chains would be feasible. By ON/OFF of one lectin, two sugar binding modes can be examined, and by ON/OFF of lectins whose number is n, recognition of $2^n$ patterns would be feasible. Accordingly, the number of lectins necessary for analyzing 7,776 sugar chain abnormalities in the hinge is theoretically 13. This number is actually theoretical, given lectins capable of significantly revealing information on sugar chain structure and position of sugar chain, but there is high possibility that the structure and position of sugar chain in the IgA hinge could be analyzed based on information from several hundreds lectins which can be blotted on the substrate. In order to obtain an useful lectin library, a lectin group reflecting differences between patient serum IgA and healthy person serum IgA most significantly can be obtained by the cluster analysis to construct an effective lectin library. By using the lectin library, differences in glycoform between IgA from patients with IgA nephropathy and serum IgA from healthy persons are analyzed by patterning (FIG. 11). In this figure, liquid 62 containing serum IgA in test tube 62 is taken by pipette 64, then dropped on library lectins 72 immobilized on lectin chip 70, washed and colored by anti-IgA, to form one pattern consisting of colored spots 74 and uncolored spots 72. The results can be summarized in Table 80 to judge the test result squalitatively and quantitatively. This figure shows that the profiling of IgA1 as glycoprotein containing a plurality of O-glycans can be easily conducted. There is also applicability not only to examination of differences from patients with severe symptoms such as chronic renal deficiency, but also to early diagnosis of potential patients with light symptoms not diagnosed as IgA nephropathy.

To confirm the foregoing, the following experiments were carried out by using materials shown in Table 2.

TABLE 2

Materials used in the experiment

Human IgA1, plasma (CALBIOCHEM #400105), diluted at 5 µg/ml with TBS (pH 7.5)
Silicic acid-digested human IgA1, plasma (CALBIOCHEM #400105), diluted at 5 µg/ml with TBS (pH 7.5)
Lysate (1 mg/ml) containing artificial lectins (Y1 to Y8, Y10) and wild type lectin
Lectin-free pFLAG-ATS lysate (1 mg/ml) as control
Mouse anti-FLAGM2 monoclonal antibody (SIGMA #F-3165) prepared by diluting a stock solution 1000-fold with 1% BSA/TBST
HRP-goat anti-mouse IgG (H + L) antibody (Zymed #62-6520) prepared by diluting a stock solution 1000-fold with 1% BSA/TBST
0.274 g ABTS/$H_2O_2$ ABTS and 10.5 g citric acid were dissolved in 500 ml Milli-Q and adjusted to pH 4.2 with NaOH, and $H_2O_2$ was added in an amount of 1/1000 to the solution just before use.
96-well ELISA plate (SUMILON #MS-8996F)

Figure 10:
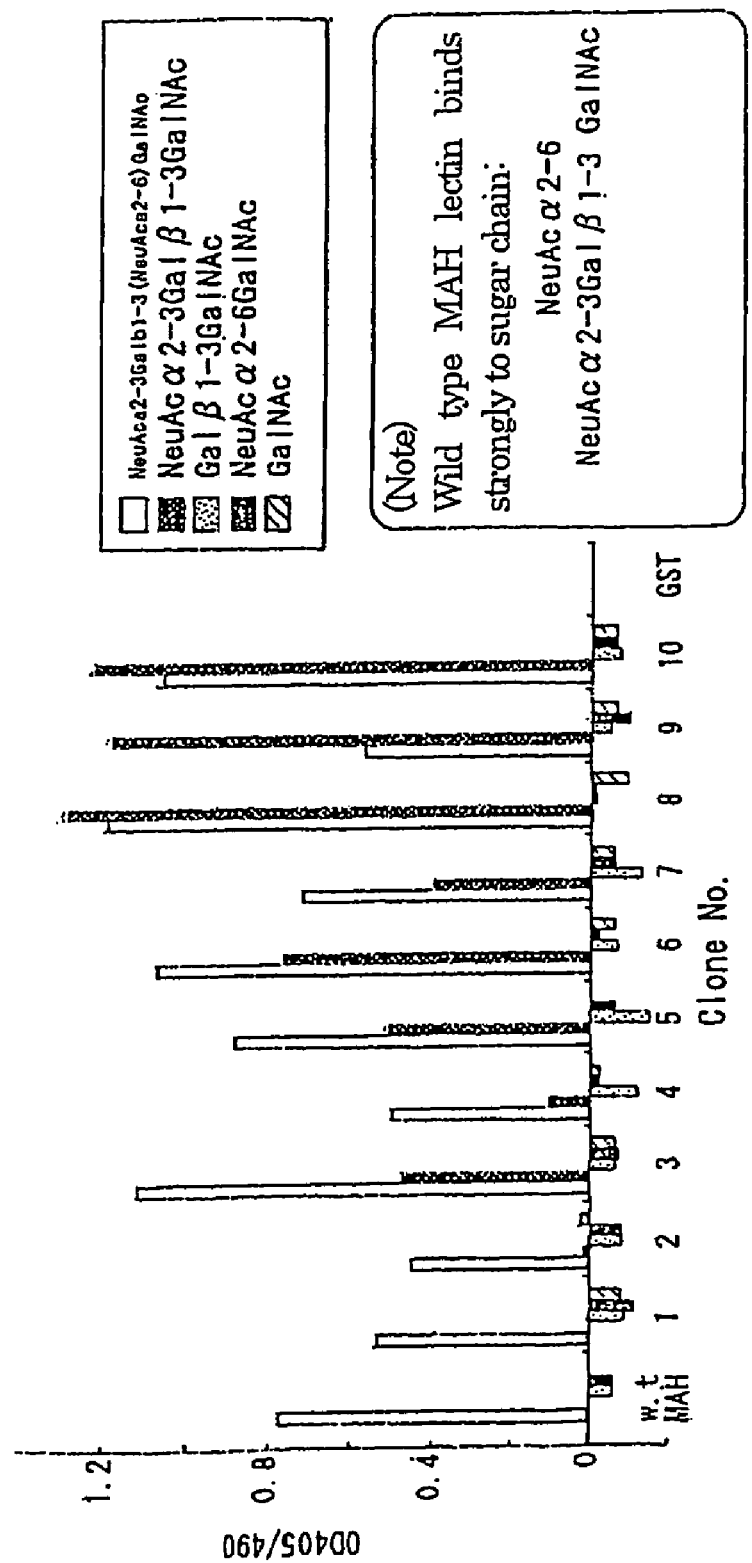
FIG. 10 shows the sugar chain specificity of clones obtained by panning with human erythrocyte.
Figure 12:
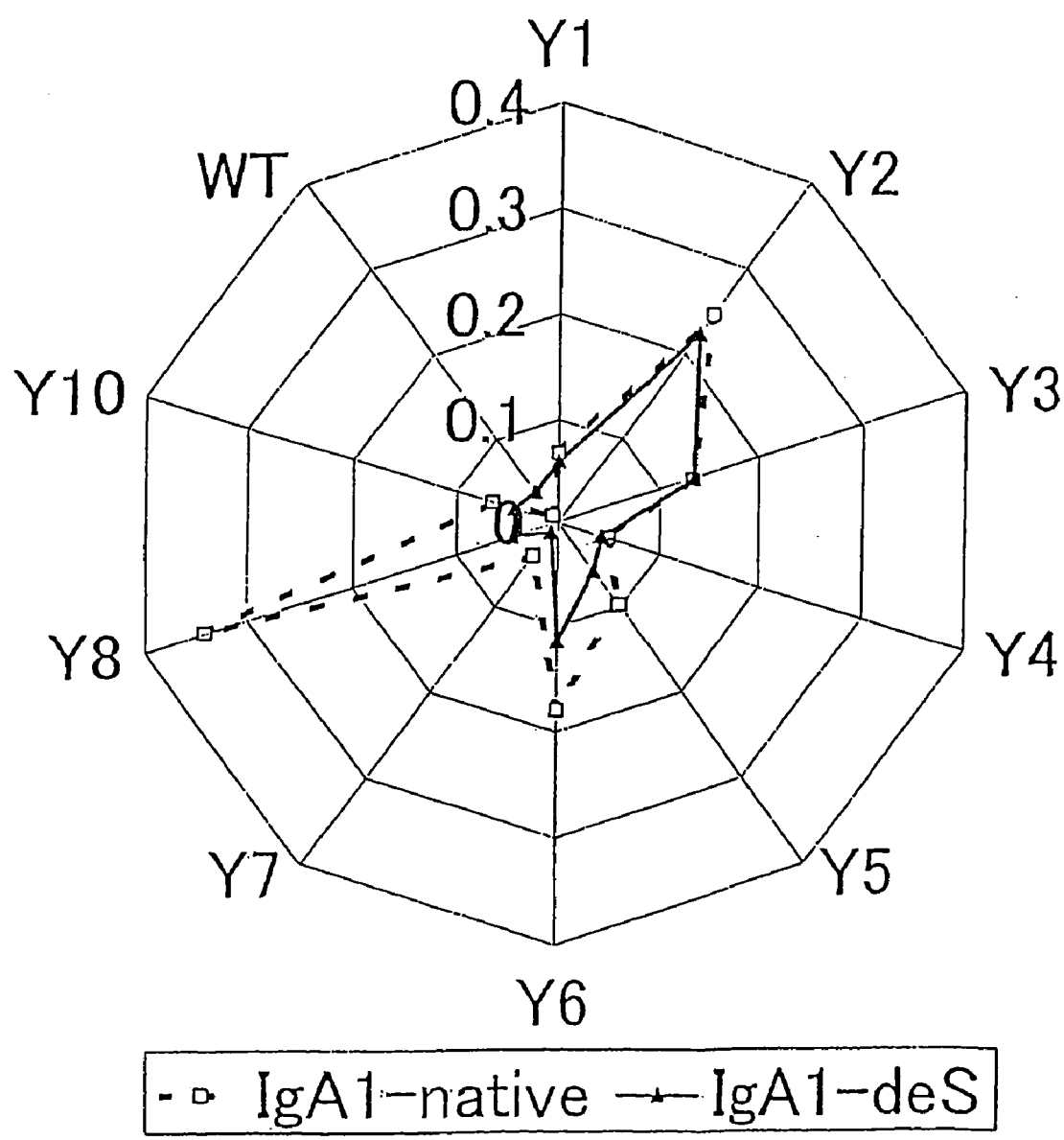
FIG. 12 shows a pattern of binding of IgA different in sugar chain glycoform to the lectin library.

Human IgA1, 50 µl (0.25 µg/well), was added to a 96-well ELISA plate and left overnight at 4° C. to immobilize the antibody onto the well. Each well was washed 3 times with TBS and then blocked with 200 µl of 3% BSA/TBS at room temperature. After 3 hours, the well was washed 3 times with TBS, and 50 µl (50 µg/well) lysate containing artificial lectins was added to each well. Peptide sequences of the lectin library used here are shown in FIG. 9. In this figure, an amino acid sequence of from amino acid at position 127 to amino acid at position 137 numbered from the N-terminus is shown, and the remainder is the same as the amino acid sequence of naturally occurring MAH lectin. As can be seen from the figure, this lectin library contained artificial lectin clones 1 to 10 (Y1 to Y10). After lectins in the lysate were bound by leaving the plate at room temperature for 2 hours, each well was washed 3 times with TBST (0.1% Tween/TBS), and 50 µl mouse anti-FLAG M2 monoclonal antibody (SIGMA #F-3165) was added to each well. After the reaction at room temperature for 30 minutes, the well was washed 3 times with TBST, and 50 µl HRP-goat anti-mouse IgG (H+L) antibody (Zymed #62-6520) was added to each well. After the reaction at room temperature for 30 minutes, the well was washed 3 times with TBST, and each well was colored with 50 µl ABTS/$H_2O_2$, and its absorbance (405, 490 nm) was measured with a plate reader. The binding of IgA1 and that of IgA1 having cleaved sugar chains to each artificial lectin were measured, and the results shown below were obtained (FIGS. 10 and 12). From this result, it was confirmed that the lectin library was useful in detection of IgA glycoform. From the result, it was revealed that the lectin library of the present invention is also effective in so-called plasmapheresis.

The IgA1 sialic acid cleavage treatment was carried out in the following manner by using the materials shown in Table 3 below.

TABLE 3

Materials used in sialic acid cleavage treatment

Human IgA1, Plasma (CALBIOCHEM #400105), 1 mg/ml
Neuraminidase (Nakalai Tesque #24229-61), 2.0 units/ml
Sodium acetate buffer [0.2 M sodium acetate (pH 5.5), 0.4 M NaCl]

To human IgA1 was added an equal volume of sodium acetate buffer, and 0.5 µl (1unit) neuraminidase was added to the solution. The mixture was reacted overnight at 37° C. in a water bath, and sialic acid in IgA1 was cleaved. TBS was added thereto to return the pH of the solution to the neutral range. Confirmation of sialic acid cleavage was confirmed by the binding to biotin-labeled purified PNA (peanut lectin #300430, Seikagaku Corporation) and MALII (*Maackia aurensis* lectin #B-1625, VECTOR).

Example 3

[Discrimination of Mesenchymal Stem Cell-Derived Osteoblast Subgroup]

Figure 13:
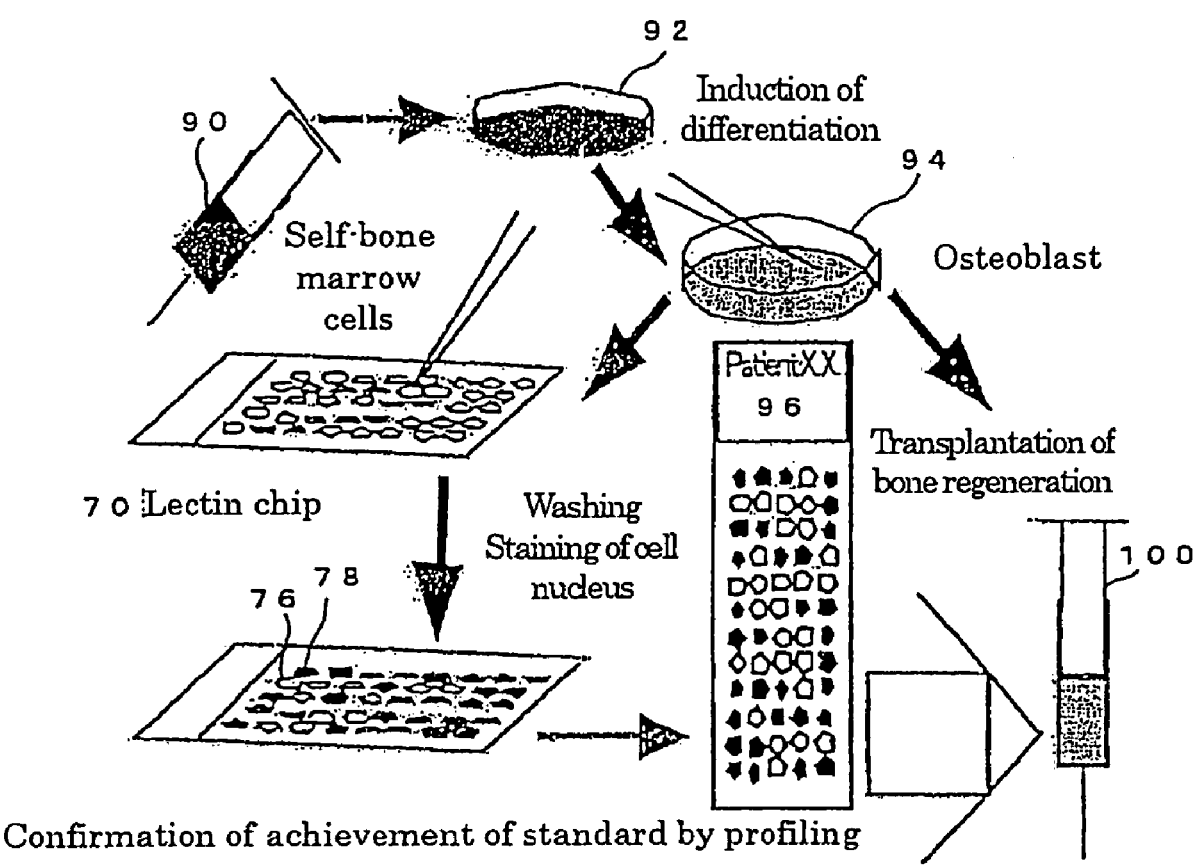
FIG. 13 shows one example of a lectin chip and a method of using the same lectin chip (with respect to profiling of differentiation of osteoblast).

One example of the method where the lectin library described above was applied to the discrimination of osteoblast or detection of subgroups different in differentiation stage is described in the order of procedures.
1) A genetically modified lectin library wherein the amino acid sequence of a sugar recognition site of MAH lectin (*Maackia aurensis* lectin) was modified is prepared.
2) Preparation of a lectin library: Lectins having a high affinity for osteoblast are selected by panning to prepare a lectin sub-library.
3) From the lectin sub-library obtained in 2) above, lectins well reflecting a differentiation stage are selected if necessary, and immobilized onto a microtiter plate to prepare a lectin plate.
4) Induction of differentiation of osteoblast and discrimination by the lectin library: Cultured mesenchymal stem cells are cultured and separated. More specifically, the mesenchymal stem cells are cultured and differentiated into osteoblast, and the cells were separated 5 days, 10 days, 15 days and 20 days respectively after the initiation of differentiation.
5) The cells separated in each point in time in the differentiation stage were analyzed by the lectin plate, and the correlation between sugar chain structures on cell surface and the ability to form bone was investigated. In measurement of the ability to form bone, the measurement of bone alkali phosphatase activity and the measurement of osteocalcin content are conducted (preparation of standard). That is, the separated cells in the form of a complex with b-TCP block for anchoring osteoblast were transplanted subcutaneously into the back of a rat, removed 4 weeks and 8 weeks after the transplantation, and measured for (i) osteocalcin content and (ii) bone alkali phosphatase activity.
6) Cells of unknown differentiation stage were analyzed by the lectin plate and compared with the standard. FIG. 13 shows that the profiling of differentiation of osteoblast is easily conducted.

Self-bone marrow cells collected by syringe 90 are placed on Petri dish 92 etc. and dropped onto the lectin chip 70 before the induction of differentiation. After washing, the cells can be stained to form one pattern consisting of colored part 78 and uncolored part 76. On the basis of this result, the osteoblast after the induction of differentiation can be transplanted via syringe 100 for bone regeneration. That is, by profiling of the resulting pattern 96, it can be confirmed that standards of bone regeneration are achieved.

The following example can be shown.

Out of cells obtained from C3H/He mouse bone marrow cells by induction of differentiation by using the materials shown in Table 4, 9-15C cells having an ability to be differentiated into myocardial cells (Makino et al.: The Journal of Clinical Investigation, March 1999, Volume 103, No. 5) and KUSA/A1 cells having an ability to be differentiated into osteoblast (Kohyama et al.: Differentiation, 2001, 68:235-244) were used in measurement of the activity of the lectin library to bind to the cells by reverse cell ELISA.

TABLE 4

Materials used in the experiment

Lysate (1 mg/ml) containing artificial lectins (Y1 to Y8, Y10) and wild type lectin
Lectin-free pFLAG-ATS lysate (1 mg/ml) as control
Cells (KUSA/A1 and 9-15C) regulated at 7.5 × $10^5$ cells/ml with 1% BSA/PBS (The cells were obtained from Dr. Umesawa, Pathology Room, Department of Medicine, Keio University)
Mouse anti-FLAG M2 monoclonal antibody (SIGMA #F-3165) diluted to 5 µg/ml with TBS (pH 7.5)
0.1% Crystal Violet (25% methanol)
96-well ELISA plate (SUMILON #MS-8996F)

Reverse cell ELISA was carried out in the following manner. 50 µl (0.25 µg/well) anti-FLAG antibody was added to each well of a 96-well ELISA plate, and left overnight at 4° C., whereby the antibody was immobilized on the well. Each well was washed 3 times with TBS and blocked for 3 hours with 200 µl of 3% BSA/TBS at room temperature. The well was washed 3 times with TBS, and 50 µl (50 µg/well) lysate containing artificial lectins was added to each well and left at room temperature for 2 hours, whereby the lectins in the lysate were bound thereto. The well was washed 3 times with TBST (0.1% Tween/TBS), and 100 µl (7.5×$10^4$ cells/well) cell suspension was added to each well. The plate was centrifuged at 1000 rpm for 5 minutes at room temperature, whereby the cells were precipitated in the bottom of the well. The plate was left at room temperature for 2 hours, to bind the cells to the lectins. The well was washed 2 or 3 times with PBS. The buffer was added so as not to contact directly with the cells. 100 µl of 0.25% glutaraldehyde/PBS was added to each well, and the cells bound to the lectin were fixed for 30 minutes.

The well was washed 3 times with TBS, and 0.2% Crystal Violet (25% methanol) was added in such a suitable amount as to immerse the cells therein and left for 5 to 10 minutes at room temperature to stain the cells. The plate was washed with water, and each well was air-dried, and 200 µl assay alcohol (10% methanol, 40% ethanol, 50% water) was added to each well.

Figure 14:
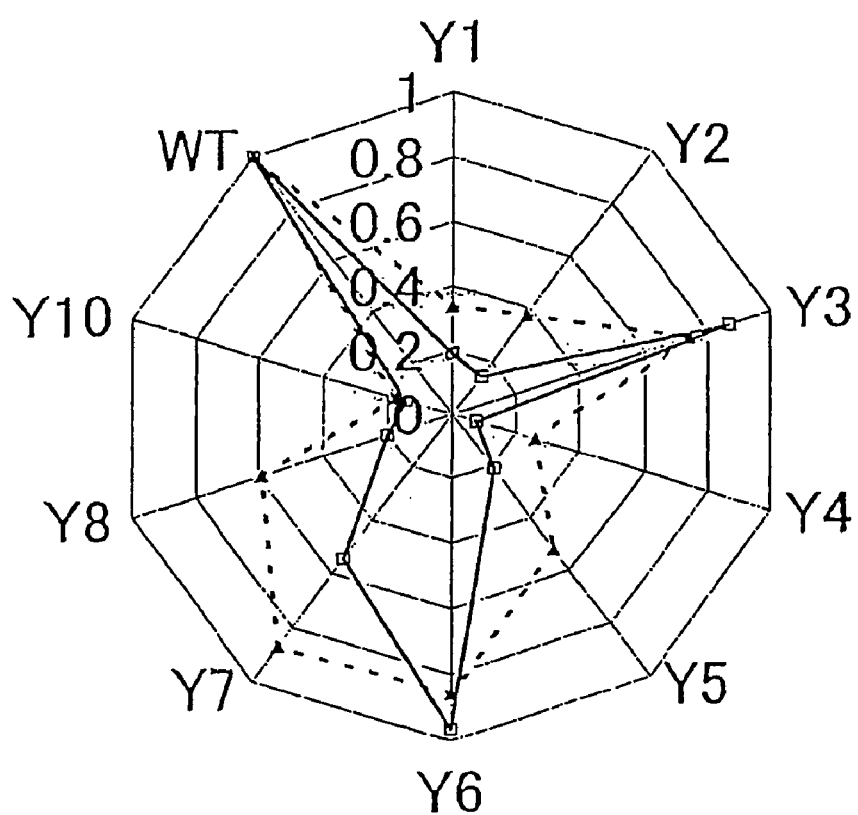
FIG. 14 shows a pattern of binding of cell subgroups derived from mesenchymal stem cells to the lectin library.
Figure 15:
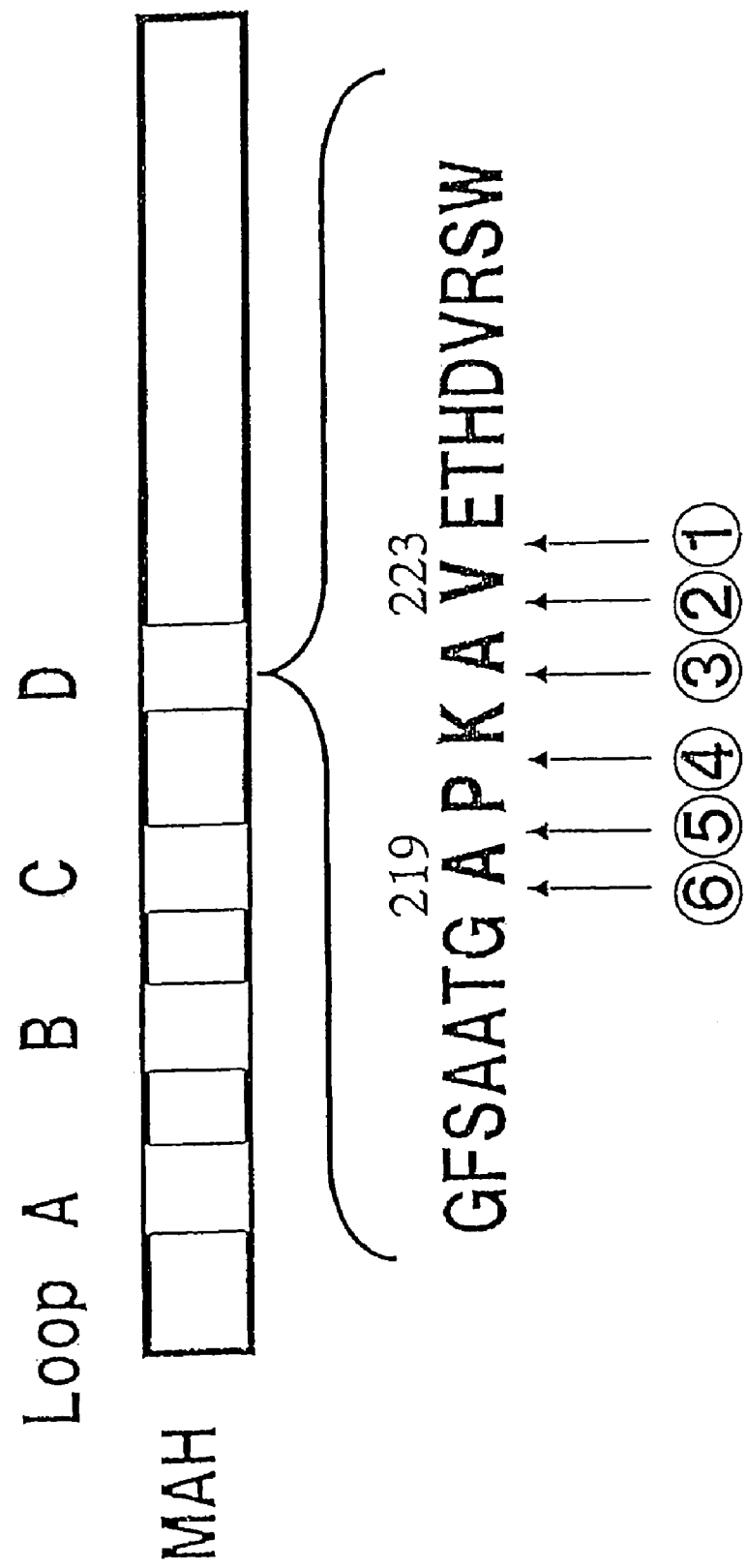
FIG. 15 shows the amino acid sequence of MAH loop D, wherein the position of amino acid inserted by modification is indicated (SEQ ID NO: 40).
Figure 16:
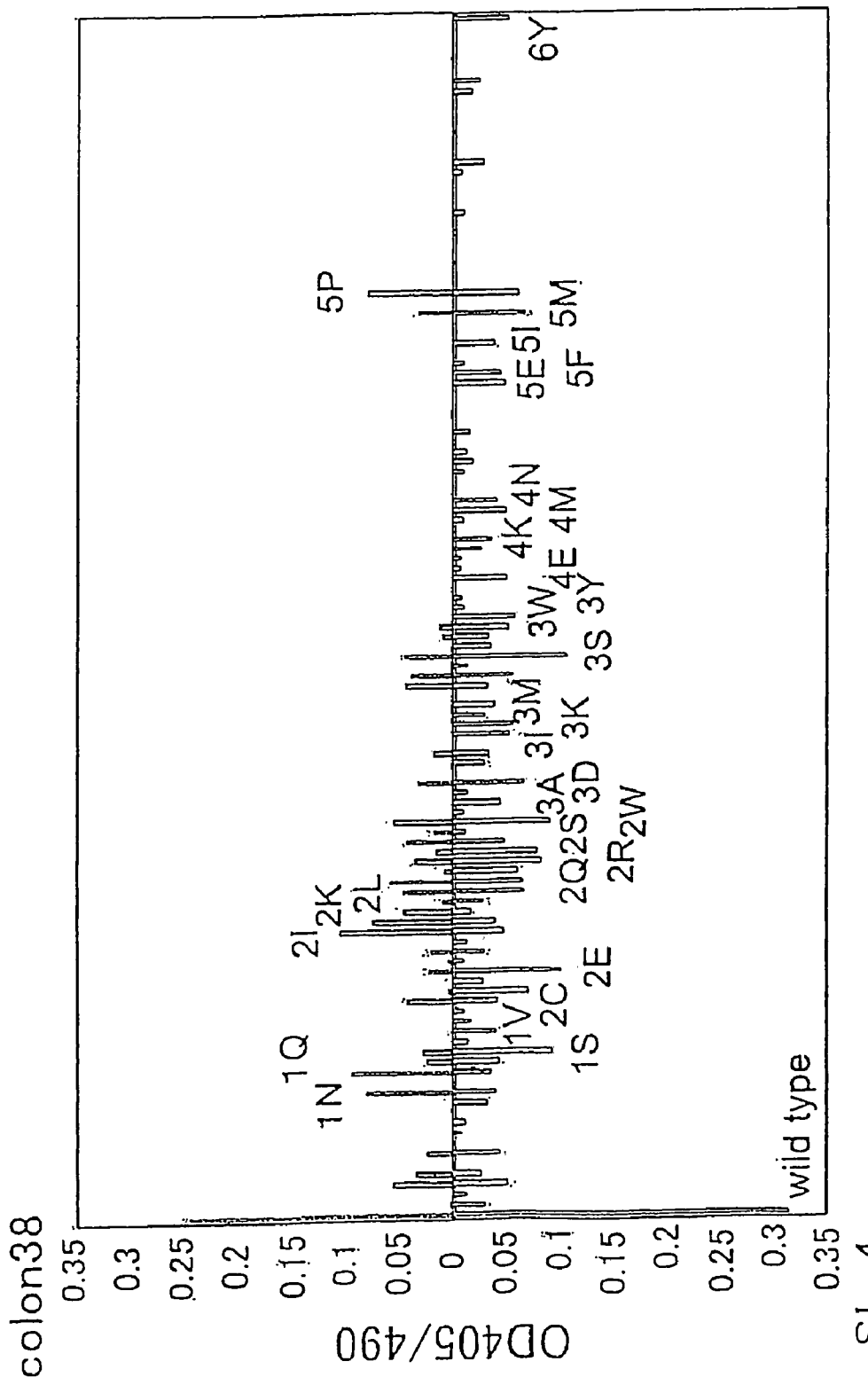
FIG. 16 shows a pattern of binding of cancer cells different in metastasis to the lectin library.

After the incubation at 37° C. for 10 minutes, the absorbance (550 nm) was measured with a plate reader. The results are shown in FIG. 14. The absorbance is shown as a relative value to that of the wild type (wt) where modification was not conducted.

From the foregoing, the lectin library was found to be useful in discrimination and identification of the cell subgroup derived from mesenchymal stem cells.

[Discrimination/Fractionation of Another Cell Subgroup Derived from Mesenchymal Stem Cells]

It was confirmed that as another cell subgroup derived from mesenchymal stem cells, KUM5 cells could be discriminated. KUM5 cells, similar to KUSA-A1 and 9-15C cells, are mouse mesenchymal stem cells containing an immortalized gene, which are differentiated into osteoblast upon induction of differentiation. Using the lysate (1 mg/ml) containing artificial lectins (Y1 to Y10) and wild type lectin, the cell subgroup was discriminated by reverse cell ELISA conducted in the same manner as above for the osteoblast subgroup derived from mesenchymal stem cells. The results are shown in FIG. 17. FIG. 17B revealed that Y-9 does not recognize KUSA-A1 or 9-15C cells and hardly binds to these cells, but binds strongly to KUM5 cells. Accordingly, it was revealed that Y-9 or the lectin library containing Y-9 can be used not only in distinguishing mesenchymal stem cells such as KUM5 cells showing differentiation into chondrocyte but also in fractionating these cells. Particularly, KUM5 cells bind specifically to chondrocyte, and can thus be used in negative selection upon differentiation of stem cells such as ES cells. Up to now, there is no specific marker for cartilage, and no antibody thereto is produced, and thus the lectin library of the present invention is highly effective for this purpose.

Example 4

Colon 38 cells are a cancer cell strain produced in vivo by chemical malignant transformation in C57BL/6 mice and established by passage in individual mice (Corbett et al.: Cancer Res 35, 2434-2439, 1975).

After colon 38 cells were injected to the spleen of a mouse, the cells transferring to the liver were subjected 4 times to a cycle of in vivo and in vitro culture, whereby an extremely highly metastatic cell strain SL4 showing highly frequent hepatic metastasis and formation in transplantation in the same place was obtained.

The binding between two cell strains different in metastatic performance and artificial lectins was analyzed. Hereinafter, the method is shown.

[Extension in loop D]

To distinguishing metastasis of cancer cells, a lectin library was prepared in the following procedure. One amino acid was inserted into 6 sites (before an amino acid sequence 219 to 224) in the center of loop D in MAH to give a library containing various lectins different in recognition specificity for sugar chain. pFLAG-ATS was used to add a FLAG tag to the N-terminus of the vector, but in the multicloning site, there was no restriction enzyme site suitable for integration of MAH, and thus Bgl II site was replaced with Spe I site according to a protocol of site directed mutagenesis. First, primers containing the site to be modified were designed to be completely complementary at the sense and antisense sides respectively. Then, PCR was carried out, and 1 μl Dpn I was added thereto, and the mixture was incubated at 37° C. for 1 hour. This DNA solution was used as such and transformed into XL1-Blue. The resulting colony was small-cultured to recover a plasmid, and its DNA sequence was read by Big Dye Terminator Cycle Sequencing to identify modified pFLAG-ATS (see Table 5).

TABLE 5

| Preparation of the vector |
|---|
| Composition of the PCR reaction solution (template (pFLAG-ATS), 1 μl; primers (pFLAG-Spe I-sense 100 ng/μl and pFLAG-Spe I-anti 100 ng/μl), each 1.25 μl; 10 × PCR buffer, 5 μl; dNTP, 1 μl; Milli Q, 40.5 μl; and pfu turbo, 1 μl) |
| PCR reaction conditions (95° C. for 30 sec and 12 cycles [95° C. for 30 sec, 55° C. for 1 min and 68° C. for 10 min]) |
| Primer sequences |
| pFLAG-Spe I-sense: 5'-ccgggtacctgcactagtagatagatgagctc (SEQ ID NO: 3) |
| FLAG-Spe I-anti: 5'-gagctcatctatctactagtgcaggtacccgg (SEQ ID NO: 4) |

[Transformation with the Vector]

Wild-type MAH cDNA and artificial cDNA derived from MAH were amplified from pFLAG-CTS by PCR and digested with restriction enzymes (conc. Xho I and conc. Spe I (manufactured by Roche)) and integrated into modified pFLAG-ATS. The product was transformed into JM109, and the resulting clone was identified by Big Dye Terminator Cycle Sequencing (see Table 6).

TABLE 6

| Transformation with the vector | |
|---|---|
| Composition of the PCR reaction solution (template 1.5 μl; primers (N-Flag-XhoI, 100 ng/μl and MAH-SpeI-anti, 100 ng/μl, each 0.5 μl; dNTP, 4 μl; 10 × PCR buffer, 5 μl; Taq Gold, 1 μl; and Milli Q 38.5 μl). | |
| The PCR reaction conditions were general (96° C. for 5 min, 30 cycles [96° C. for 1 min, 55° C. for 1 min, 72° C. for 2 min] and 72° C. for 5 min) | |
| Primer sequences | |
| pFLAG-XhoI: 5'-ccaggtgaaactgctcgagtcagatg | (SEQ ID NO: 5) |
| MAH-Spe I anti: 5'-tgggcaactagttgcagtgtaacgtgcg | (SEQ ID NO: 6) |
| Primer sequences used in sequencing | |
| N-26: 5'-catcataacggttctggcaaatattc | (SEQ ID NO: 7) |
| Loop D-Seq: 5'-gttaatagcatctctagtttaccc | (SEQ ID NO: 8) |

[Extension of loop D]

Using restriction enzymes (conc. Xho I and conc. Bgl II), clones were prepared in the same manner as described above, and isolated and identified. Clones which could not be isolated in modification using primers for random insertion of amino acid were isolated and identified by individually designing primers (see Table 7).

[Isolation and Identification of Clones Having Modified MAH cDNA]

A multicloning site Bgl II site could be converted into Spe I site. There was no mutation other than the target region. Theroretically predicted 120 modified MAHs could be isolated and identified.

TABLE 7

| | | |
|---|---|---|
| Primers used in random modification | | |
| N-Flag-XhoI: | 5'-ccaggtgaaactgctcgagtcagatg | (SEQ ID NO: 5) |
| LLD3: | 5'-ctacaagatctaacatcgtgggtttcaactgcmnntttaggagcacccgtggcagcaga | (SEQ ID NO: 9) |
| LLD4: | 5'-ctacaagatctaacatcgtgggtttcaactgctttmnnaggagcacccgtggcagcaga | (SEQ ID NO: 10) |
| LLD5: | 5'-ctacaagatctaacatcgtgggtttcaactgctttaggmnnagcacccgtggcagcaga | (SEQ ID NO: 11) |
| LLD6: | 5'-ctacaagatctaacatcggtgggtttcaactgctttaggagcmnnaccgtggcagcaga | (SEQ ID NO: 12) |
| Individually designed primers | | |
| MAH loop D-1Phe: | 5'-ctacaagatctaacatcgtgggtttcaaaaactgctttaggagcacccgtggcagcaga | (SEQ ID NO: 13) |
| MAH loop D-2Asp: | 5'-ctacaagatctaacatcgtgggtttcaacatctgctttaggagcacccgtggcagcaga | (SEQ ID NO: 14) |
| MAH loop D-3Cys: | 5'-ctacaagatctaacatcgtgggtttcaactgcacatttaggagcacccgtggcagcaga | (SEQ ID NO: 15) |
| MAH loop D-4Asp: | 5'-ctacaagatctaacatcgtgggtttcaactgctttatcaggagcacccgtggcagcaga | (SEQ ID NO: 16) |
| MAH loop D-6Phe: | 5'-ctacaagatctaacatcgtgggtttcaactgctttaggagcaaaacccgtggcagcaga | (SEQ ID NO: 17) |

[Change of the Protocol of Big Dye Terminator Cycle Sequencing]

In this sequencing, the known protocol was altered. This alteration is shown in Table 8.

TABLE 8

| Change in protocol |
|---|
| Composition of PCR solution:<br>5 × Sequencing Buffer 2 μl → 10 × PCR buffer 2 μl<br>Solvent dissolving the sequence sample after preparation by ethanol precipitation<br>HI-Di formamide 20 μl → Milli Q 20 μl |

[*E. coli* Lysate (Preparation of Lysate)]

The *E. coli* isolated in HEM (highly enriched medium) containing carbenicillin was short-cultured overnight. On the next day, 200 μl *E. coli* short-cultured was added to a medium consisting of 20 ml HEM, 20 μl $CaCl_2$ (1 M), 20 μl $MnCl_2$ (1M) and 81.7 μl $MgCl_2$ (4.9 M), and then pre-cultured for 3 hours. 200 μl of 100 mM IPTG was added thereto, the cells were cultured for induction for 3 hours. Then, the *E. coli* was recovered by centrifugation at 9,500 rpm for 10 minutes and suspended in 200 μl TBS and stored at −80° C. On a later day, the *E. coli* was subjected 5 times to freezing (liquid nitrogen) and thawing (water bath at 37° C.), and then centrifuged at 15,000 rpm for 20 minutes to recover the supernatant as lysate. This lysate was quantified for its protein and then stored at −80° C. Before use, the lysate was diluted to a protein concentration of 1 mg/ml and stored at 4° C.

[Detection of Flag Fusion Protein by SDS-PAGE and Western Blotting]

To examine whether the modified FLAG-MAH was present in the lysate, a sample was selected suitably and s ubjected to SDS-PAGE and Western blotting. In staining with antibody, anti-MAH rabbit polyclonal antibody or anti-FLAG M2 monoclonal antibody was used as the primary antibody, and AP-goat anti-rabbit IgG antibody and AP-goat anti-mouse IgG antibody were used as the secondary antibody, and the sample was colored with an ABC kit.

The expression of FLAG-modified lectin as flag fusion protein or as MAH could be confirmed.

[Discrimination of Two Kinds of Cancer Cells]

Poly-L-lysine (1 μg/well) was put into a 96-well ELISA plate (and incubated at 37° C. for 30 minutes), and a cell suspension ($10^5$ cells/well; Colon-38, SL-4, Caco-2, differentiated Caco-2) was added thereto, and the cells were immobilized by glutaraldehyde (25%) (1 μg/well) onto the plate (left at room temperature for 30 minutes). TBS was put into each well on the plate having the cells immobilized thereon and then stored at 4° C., each well was blocked with 3% BSA/TBS (shaken at room temperature for 3 hours), and the lysate (50 μg/well) containing the modified MAH lectins prepared above was added thereto (and shaken at room temperature for 2 hours). Anti-FLAG M2monoclonal antibody (1000-fold dilution, 50 μl/well) was used as the primary antibody, and HRP-goat anti-mouse IgG antibody (1000-fold dilution, 50 μl/well) was used as the secondary antibody (both of which were shaken at room temperature for 30 minutes). Each sample was colored with ABTS/$H_2O_2$ (50 μl/well) and measured for $OD_{405/490}$.

FIG. 16 shows the binding of 120 kinds of modified lectins to colon 38 or SL 4. The colon 38 or SL 4 are two kinds of cancer cell lines having the same origin. In the graph, 1Q means that in FIG. 15 [sic], glutamine is inserted in to position 1; 2C means that cysteine is inserted into position 2; 3D means that aspartic acid is inserted into position 3; 3S means that serine is inserted into position 3; and 4N means that asparagine is inserted into position 4. That is, "nX" generally means that in FIG. 5, amino acid "X" is inserted into position "n". The reason that the difference in binding to cells different in properties is considered attributable to a difference in sugar chains on cell surface, and accordingly the traits of sugar chains or cells can be judged by using these lectin groups. Particularly, the cells etc. having the same origin, such as colon 38 and SL 4, have lectins different in binding property, and it was revealed that a library capable of clarifying this difference and distinguishing the metastatic performance of the cancer cells can be prepared.

INDUSTRIAL APPLICABILITY

According to the present invention, it was found that a lectin library reflects differences in serodiagnosis and in the type and differentiation stage of cells and is useful in a diagnostic method.

By analyzing sugar chains or carbohydrates on cell surface by this new method, cell identification having depended on only gene expression can be accurately conducted, thus contributing to development of cell transplant and cell therapy. This study succeeded in expressing an artificial lectin library on the surface of phagemid type phage. Because a method of selecting lectins different in specificity from a modified lectin library was established, it can be expected that lectins having a novel chain sugar specificity which is absent in existing lectins or monoclonal antibodies can be obtained by using this system.

Further, the lectin library of the present invention can be used to provide a tool for detection of IgA glycoform or for discrimination and identification of osteoblast subgroup. That is, there can also be provided a diagnostic reagent by which glycoforms of various serum proteins including IgA can be easily and rapidly diagnosed in vitro, and there can also be provided a standard design tool for guaranteeing qualities of cells necessary for a practical stage of regenerative medicine or cell therapy. The lectin library can be applied for example to early finding of diseases, to accurate understanding of morbid states or to therapeutic agent and prophylactic agent in cases where there occur glycosylation of immunoglobulin in rheumatism or autoimmune diseases, or glycosylation of specific hormones (change in sugar chains of chorionic gonadotropin in ovary cancer) or proteins (change in sugar chains of alpha fetoprotein [phonetic] upon change from hepatitis to hepatoma).

Because an antibody is characterized by production arising from differences in species, the preparation of a specific antibody to fibroblast is difficult so that on the fibroblast derived from bone marrow, there is none of so-called cell surface marker, and there is no method of directly assaying osteoblast, and even in the field where bioassays using animals or indirect assays reflecting the activity of osteoblast are mainly used at present, discrimination/identification of osteoblast, particularly discrimination/identification of subgroups different in differentiation stage is considered feasible by a lectin chip using the lectin library of the present invention. There is extremely high possibility that the lectin library can be applied by the same approach to dendritic cells derived from bone marrow and vascular endothelial cells derived from bone marrow, and can be a standard tool for securing qualities of cells used in regenerative therapy.

In network of cancer remote diagnosis at present, pathological diagnosis is mainly used, but the addition of information on genetic expression is examined, and in view of the finding that O-binding sugar chains are related closely to interaction among cells, infiltration with cells, adhesion etc., more detailed cancer remote diagnosis can be examined by adding information on sugar chains.

The invention claimed is:

1. A lectin library for discriminating glycoproteins or cells, diagnosing serum or cells or fractionating glycoproteins or cells, which comprises a recombinant *Maackia amurensis* hemagglutinin (MAH) lectin molecule having a sugar chain binding region comprising the amino acid sequence selected from the group consisting of SEQ ID Nos: 22 and 30.

2. The lectin library according to claim 1, wherein the discrimination of cells is of discrimination of an osteoblast subgroup or discrimination of a cell subgroup derived from mesenchymal stem cells.

3. The lectin library of claim 1 wherein the recombinant MAII lectin molecule has a sugar chain binding region comprising the amino acid sequence set forth in SEQ ID No: 30.

* * * * *

SEQUENCE LISTING

<160> NUMBER OF SEQ ID NOS: 31

<210> SEQ ID NO 1
<211> LENGTH: 950
<212> TYPE: DNA
<213> ORGANISM: Maackia amurensis
<220> FEATURE:
<221> NAME/KEY: CDS
<222> LOCATION: (4)..(858)
<223> OTHER INFORMATION:

<400> SEQUENCE: 1

```
gcc atg gct act tcc aac tca aaa cca act caa gtc ctt ctt gcc acc        48
    Met Ala Thr Ser Asn Ser Lys Pro Thr Gln Val Leu Leu Ala Thr
    1               5                   10                  15 ttc tta act ttc ttc ctt ttg cta ctc aac aac gta aac tca tca gat        96
Phe Leu Thr Phe Phe Leu Leu Leu Leu Asn Asn Val Asn Ser Ser Asp
                20                  25                  30 gag ctt tct ttt acc atc aac aat ttc atg cca aat caa ggc gat cta       144
Glu Leu Ser Phe Thr Ile Asn Asn Phe Met Pro Asn Gln Gly Asp Leu
            35                  40                  45 ctc ttc caa ggt gta gcc act gtt tca cca aca ggg gta tta caa ctt       192
Leu Phe Gln Gly Val Ala Thr Val Ser Pro Thr Gly Val Leu Gln Leu
        50                  55                  60 acc agc gaa gaa aac ggt caa ccc ctg gag tat tct gtt ggc aga gct       240
Thr Ser Glu Glu Asn Gly Gln Pro Leu Glu Tyr Ser Val Gly Arg Ala
    65                  70                  75 cta tat act gcc cct gtg cgc att tgg gac agt acc act ggc gcc gta       288
Leu Tyr Thr Ala Pro Val Arg Ile Trp Asp Ser Thr Thr Gly Ala Val
```

```
                80                  85                  90                  95
gca agc ttc tcc act tcc ttc acc ttt gtt gtg aaa gca gct agg gga         336
Ala Ser Phe Ser Thr Ser Phe Thr Phe Val Val Lys Ala Ala Arg Gly
                100                 105                 110 gct tct gac ggt tta gcc ttc ttt ctt gca cca cct gat tct cag atc         384
Ala Ser Asp Gly Leu Ala Phe Phe Leu Ala Pro Pro Asp Ser Gln Ile
            115                 120                 125 cct tcg ggc agc gta tcg aaa tac cta gga ctt ttt aac aac tca aat         432
Pro Ser Gly Ser Val Ser Lys Tyr Leu Gly Leu Phe Asn Asn Ser Asn
            130                 135                 140 tcc gat agt tcc aac caa att gtt gct gta gag ttt gac act tac ttc         480
Ser Asp Ser Ser Asn Gln Ile Val Ala Val Glu Phe Asp Thr Tyr Phe
145                 150                 155 ggc cat agt tat gat ccc tgg gat cca aat tat cga cat atc gga att         528
Gly His Ser Tyr Asp Pro Trp Asp Pro Asn Tyr Arg His Ile Gly Ile
160                 165                 170                 175 gat gtc aac ggt att gag tcg ata aaa act gtg caa tgg gat tgg att         576
Asp Val Asn Gly Ile Glu Ser Ile Lys Thr Val Gln Trp Asp Trp Ile
                180                 185                 190 aac ggc gga gtt gcc ttt gct acc ata acc tat cta gct ccc aac aaa         624
Asn Gly Gly Val Ala Phe Ala Thr Ile Thr Tyr Leu Ala Pro Asn Lys
            195                 200                 205 acg tta ata gca tct cta gtt tac cct tcc aat caa aca agt ttc att         672
Thr Leu Ile Ala Ser Leu Val Tyr Pro Ser Asn Gln Thr Ser Phe Ile
            210                 215                 220 gtc gct gct tct gtt gat ttg aag gga atc ctc cct gag tgg gtt aga         720
Val Ala Ala Ser Val Asp Leu Lys Gly Ile Leu Pro Glu Trp Val Arg
225                 230                 235 gtt ggt ttc tct gct gcc acg ggt gct cct aaa gca gtt gaa acc cac         768
Val Gly Phe Ser Ala Ala Thr Gly Ala Pro Lys Ala Val Glu Thr His
240                 245                 250                 255 gat gtt cgt tcc tgg tct ttc acg tca act ttg gaa gcc aac agc cct         816
Asp Val Arg Ser Trp Ser Phe Thr Ser Thr Leu Glu Ala Asn Ser Pro
                260                 265                 270 gct gat gtg gat aat aat gtg cat atc gca cgt tac act gca                 858
Ala Asp Val Asp Asn Asn Val His Ile Ala Arg Tyr Thr Ala
            275                 280                 285 tgatctcgtg agctttcgta tgtattaggt gtttatgtaa attaaataaa aatgacctga       918
aataatggtt atcggcgcag ctatacaaaa at                                     950

<210> SEQ ID NO 2
<211> LENGTH: 285
<212> TYPE: PRT
<213> ORGANISM: Maackia amurensis

<400> SEQUENCE: 2

Met Ala Thr Ser Asn Ser Lys Pro Thr Gln Val Leu Leu Ala Thr Phe
1               5                   10                  15

Leu Thr Phe Phe Leu Leu Leu Asn Val Asn Ser Ser Asp Glu
            20                  25                  30

Leu Ser Phe Thr Ile Asn Asn Phe Met Pro Asn Gln Gly Asp Leu Leu
        35                  40                  45

Phe Gln Gly Val Ala Thr Val Ser Pro Thr Gly Val Leu Gln Leu Thr
    50                  55                  60

Ser Glu Glu Asn Gly Gln Pro Leu Glu Tyr Ser Val Gly Arg Ala Leu
65                  70                  75                  80

Tyr Thr Ala Pro Val Arg Ile Trp Asp Ser Thr Thr Gly Ala Val Ala
                85                  90                  95
```

```
Ser Phe Ser Thr Ser Phe Thr Phe Val Val Lys Ala Ala Arg Gly Ala
                100                 105                 110

Ser Asp Gly Leu Ala Phe Phe Leu Ala Pro Pro Asp Ser Gln Ile Pro
            115                 120                 125

Ser Gly Ser Val Ser Lys Tyr Leu Gly Leu Phe Asn Asn Ser Asn Ser
        130                 135                 140

Asp Ser Ser Asn Gln Ile Val Ala Val Glu Phe Asp Thr Tyr Phe Gly
145                 150                 155                 160

His Ser Tyr Asp Pro Trp Asp Pro Asn Tyr Arg His Ile Gly Ile Asp
                165                 170                 175

Val Asn Gly Ile Glu Ser Ile Lys Thr Val Gln Trp Asp Trp Ile Asn
            180                 185                 190

Gly Gly Val Ala Phe Ala Thr Ile Thr Tyr Leu Ala Pro Asn Lys Thr
        195                 200                 205

Leu Ile Ala Ser Leu Val Tyr Pro Ser Asn Gln Thr Ser Phe Ile Val
    210                 215                 220

Ala Ala Ser Val Asp Leu Lys Gly Ile Leu Pro Glu Trp Val Arg Val
225                 230                 235                 240

Gly Phe Ser Ala Ala Thr Gly Ala Pro Lys Ala Val Glu Thr His Asp
                245                 250                 255

Val Arg Ser Trp Ser Phe Thr Ser Thr Leu Glu Ala Asn Ser Pro Ala
            260                 265                 270

Asp Val Asp Asn Asn Val His Ile Ala Arg Tyr Thr Ala
        275                 280                 285

<210> SEQ ID NO 3
<211> LENGTH: 32
<212> TYPE: DNA
<213> ORGANISM: Artificial
<220> FEATURE:
<223> OTHER INFORMATION: Tag Primer pFLAG-Spe I-sense

<400> SEQUENCE: 3
ccgggtacct gcactagtag atagatgagc tc                               32

<210> SEQ ID NO 4
<211> LENGTH: 32
<212> TYPE: DNA
<213> ORGANISM: Artificial
<220> FEATURE:
<223> OTHER INFORMATION: Tag Primer pFLAG-Spe I-anti

<400> SEQUENCE: 4
gagctcatct atctactagt gcaggtaccc gg                               32

<210> SEQ ID NO 5
<211> LENGTH: 26
<212> TYPE: DNA
<213> ORGANISM: Artificial
<220> FEATURE:
<223> OTHER INFORMATION: pFLAG-XhoI

<400> SEQUENCE: 5
ccaggtgaaa ctgctcgagt cagatg                                      26

<210> SEQ ID NO 6
<211> LENGTH: 28
<212> TYPE: DNA
<213> ORGANISM: Artificial
<220> FEATURE:
```

<223> OTHER INFORMATION: Primer MAH-Spe I-anti

<400> SEQUENCE: 6
tgggcaacta gttgcagtgt aacgtgcg                                28

<210> SEQ ID NO 7
<211> LENGTH: 26
<212> TYPE: DNA
<213> ORGANISM: Artificial
<220> FEATURE:
<223> OTHER INFORMATION: Analyzing Primer N-26

<400> SEQUENCE: 7
catcataacg gttctggcaa atattc                                  26

<210> SEQ ID NO 8
<211> LENGTH: 24
<212> TYPE: DNA
<213> ORGANISM: Artificial
<220> FEATURE:
<223> OTHER INFORMATION: Sequence Primer Loop D-Seq

<400> SEQUENCE: 8
gttaatagca tctctagttt accc                                    24

<210> SEQ ID NO 9
<211> LENGTH: 59
<212> TYPE: DNA
<213> ORGANISM: Artificial
<220> FEATURE:
<223> OTHER INFORMATION: Inert Primer LLD3
<220> FEATURE:
<221> NAME/KEY: misc_feature
<222> LOCATION: (34)..(35)
<223> OTHER INFORMATION: n is a or c or g or t or u.
<220> FEATURE:
<221> NAME/KEY: misc_feature
<222> LOCATION: (33)..(33)
<223> OTHER INFORMATION: m is a or c.

<400> SEQUENCE: 9
ctacaagatc taacatcgtg ggtttcaact gcmnntttag gagcacccgt ggcagcaga    59

<210> SEQ ID NO 10
<211> LENGTH: 59
<212> TYPE: DNA
<213> ORGANISM: Artificial
<220> FEATURE:
<223> OTHER INFORMATION: Insert Primer LLD4
<220> FEATURE:
<221> NAME/KEY: misc_feature
<222> LOCATION: (37)..(38)
<223> OTHER INFORMATION: n is a or c or g or t or u.
<220> FEATURE:
<221> NAME/KEY: misc_feature
<222> LOCATION: (36)..(36)
<223> OTHER INFORMATION: m is a or c.

<400> SEQUENCE: 10
ctacaagatc taacatcgtg ggtttcaact gctttmnnag gagcacccgt ggcagcaga    59

<210> SEQ ID NO 11
<211> LENGTH: 59
<212> TYPE: DNA
<213> ORGANISM: Artificial
<220> FEATURE:
<223> OTHER INFORMATION: Insert Primer LLD5
<220> FEATURE:
<221> NAME/KEY: misc_feature

```
<222> LOCATION: (40)..(41)
<223> OTHER INFORMATION: n is a or c or g or t or u.
<220> FEATURE:
<221> NAME/KEY: misc_feature
<222> LOCATION: (39)..(39)
<223> OTHER INFORMATION: m is a or c.

<400> SEQUENCE: 11
ctacaagatc taacatcgtg ggtttcaact gctttaggmn nagcacccgt ggcagcaga      59

<210> SEQ ID NO 12
<211> LENGTH: 59
<212> TYPE: DNA
<213> ORGANISM: Artificial
<220> FEATURE:
<223> OTHER INFORMATION: Insert Primer LLD6
<220> FEATURE:
<221> NAME/KEY: misc_feature
<222> LOCATION: (43)..(44)
<223> OTHER INFORMATION: n is a or c or g or t or u.
<220> FEATURE:
<221> NAME/KEY: misc_feature
<222> LOCATION: (42)..(42)
<223> OTHER INFORMATION: m is a or c.

<400> SEQUENCE: 12
ctacaagatc taacatcgtg ggtttcaact gctttaggag cmnnacccgt ggcagcaga      59

<210> SEQ ID NO 13
<211> LENGTH: 59
<212> TYPE: DNA
<213> ORGANISM: Artificial
<220> FEATURE:
<223> OTHER INFORMATION: Insert Primer MAH loop D-1 Phe

<400> SEQUENCE: 13
ctacaagatc taacatcgtg ggtttcaaaa actgctttag gagcacccgt ggcagcaga      59

<210> SEQ ID NO 14
<211> LENGTH: 59
<212> TYPE: DNA
<213> ORGANISM: Artificial
<220> FEATURE:
<223> OTHER INFORMATION: Insert Primer MAH loop D-2 Asp

<400> SEQUENCE: 14
ctacaagatc taacatcgtg ggtttcaaca tctgctttag gagcacccgt ggcagcaga      59

<210> SEQ ID NO 15
<211> LENGTH: 59
<212> TYPE: DNA
<213> ORGANISM: Artificial
<220> FEATURE:
<223> OTHER INFORMATION: Insert Primer MAH loop D-3 Cys

<400> SEQUENCE: 15
ctacaagatc taacatcgtg ggtttcaact gcacatttag gagcacccgt ggcagcaga      59

<210> SEQ ID NO 16
<211> LENGTH: 59
<212> TYPE: DNA
<213> ORGANISM: Artificial
<220> FEATURE:
<223> OTHER INFORMATION: Insert Primer MAH loop D-4 Asp

<400> SEQUENCE: 16
ctacaagatc taacatcgtg ggtttcaact gctttatcag gagcacccgt ggcagcaga      59
```

```
<210> SEQ ID NO 17
<211> LENGTH: 59
<212> TYPE: DNA
<213> ORGANISM: Artificial
<220> FEATURE:
<223> OTHER INFORMATION: Insert Primer MAH loop D-6 Phe

<400> SEQUENCE: 17
ctacaagatc taacatcgtg ggtttcaact gctttaggag caaaacccgt ggcagcaga      59

<210> SEQ ID NO 18
<211> LENGTH: 40
<212> TYPE: DNA
<213> ORGANISM: Artificial
<220> FEATURE:
<223> OTHER INFORMATION: Primer EcoRI-S

<400> SEQUENCE: 18
ccgatagttc caaccaaatt gttgctgtag aattcgacac                            40

<210> SEQ ID NO 19
<211> LENGTH: 21
<212> TYPE: DNA
<213> ORGANISM: Artificial
<220> FEATURE:
<223> OTHER INFORMATION: BamHI reverse primer

<400> SEQUENCE: 19
cacaaacgaa tggggatcca c                                                21

<210> SEQ ID NO 20
<211> LENGTH: 26
<212> TYPE: DNA
<213> ORGANISM: Artificial
<220> FEATURE:
<223> OTHER INFORMATION: N-Flag-XhoI primer

<400> SEQUENCE: 20
ccaggtgaaa ctgctcgagt cagatg                                           26

<210> SEQ ID NO 21
<211> LENGTH: 23
<212> TYPE: DNA
<213> ORGANISM: Artificial
<220> FEATURE:
<223> OTHER INFORMATION: Antisense primer Flag-Sal I for PCR

<400> SEQUENCE: 21
gtggtcgact gcagtgtaac gtg                                              23

<210> SEQ ID NO 22
<211> LENGTH: 11
<212> TYPE: PRT
<213> ORGANISM: Artificial
<220> FEATURE:
<223> OTHER INFORMATION: Clone 1

<400> SEQUENCE: 22

Asp Thr Tyr Phe Gly His Gly Tyr Asp Pro Trp
1               5                   10

<210> SEQ ID NO 23
<211> LENGTH: 11
<212> TYPE: PRT
<213> ORGANISM: Artificial
<220> FEATURE:
```

-continued

<223> OTHER INFORMATION: Clone 2

<400> SEQUENCE: 23

Asp Thr Tyr Phe Arg His Asn Tyr Asp Pro Trp
1               5                   10

<210> SEQ ID NO 24
<211> LENGTH: 11
<212> TYPE: PRT
<213> ORGANISM: Artificial
<220> FEATURE:
<223> OTHER INFORMATION: Clone 3

<400> SEQUENCE: 24

Asp Thr Tyr Phe Ser His Asn Tyr Asp Pro Trp
1               5                   10

<210> SEQ ID NO 25
<211> LENGTH: 11
<212> TYPE: PRT
<213> ORGANISM: Artificial
<220> FEATURE:
<223> OTHER INFORMATION: Clone 4

<400> SEQUENCE: 25

Asp Thr Tyr Phe Gly His Arg Tyr Asp Pro Trp
1               5                   10

<210> SEQ ID NO 26
<211> LENGTH: 11
<212> TYPE: PRT
<213> ORGANISM: Artificial
<220> FEATURE:
<223> OTHER INFORMATION: Clone 5

<400> SEQUENCE: 26

Asp Thr Tyr Phe Gly His Val Tyr Asp Pro Trp
1               5                   10

<210> SEQ ID NO 27
<211> LENGTH: 11
<212> TYPE: PRT
<213> ORGANISM: Artificial
<220> FEATURE:
<223> OTHER INFORMATION: Clone 6

<400> SEQUENCE: 27

Asp Thr Tyr Phe Ala His Asn Tyr Asp Pro Trp
1               5                   10

<210> SEQ ID NO 28
<211> LENGTH: 11
<212> TYPE: PRT
<213> ORGANISM: Artificial
<220> FEATURE:
<223> OTHER INFORMATION: Clone 7

<400> SEQUENCE: 28

Asp Thr Tyr Phe Gly His Leu Tyr Asp Pro Trp
1               5                   10

<210> SEQ ID NO 29
<211> LENGTH: 11
<212> TYPE: PRT
<213> ORGANISM: Artificial
<220> FEATURE:
<223> OTHER INFORMATION: Clone 8

```
<400> SEQUENCE: 29

Asp Thr Tyr Phe Gly His Asp Tyr Asp Pro Trp
1               5                   10

<210> SEQ ID NO 30
<211> LENGTH: 11
<212> TYPE: PRT
<213> ORGANISM: Artificial
<220> FEATURE:
<223> OTHER INFORMATION: Clone 9

<400> SEQUENCE: 30

Asp Thr Tyr Phe Tyr His Asn Tyr Asp Pro Trp
1               5                   10

<210> SEQ ID NO 31
<211> LENGTH: 11
<212> TYPE: PRT
<213> ORGANISM: Artificial
<220> FEATURE:
<223> OTHER INFORMATION: Clone 10

<400> SEQUENCE: 31

Asp Thr Tyr Phe Gly His Trp Tyr Asp Pro Trp
1               5                   10
```